United States Patent
Yuan

(10) Patent No.: US 11,872,092 B2
(45) Date of Patent: Jan. 16, 2024

(54) METHODS FOR SURGICAL GUIDANCE IN BREAST CANCER SURGERY AND LYMPH NODE DISSECTION USING TWO OR MORE IMPLANTATION DEVICES COMPRISING A CAPSULE AND A POPULATION OF ULTRASOUND-SWITCHABLE FLUOROPHORES INCORPORATED IN THE CAPSULE

(71) Applicant: Board of Regents, The University of Texas System, Austin, TX (US)

(72) Inventor: Baohong Yuan, Arlington, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 17/095,121

(22) Filed: Nov. 11, 2020

(65) Prior Publication Data

US 2021/0153971 A1  May 27, 2021

Related U.S. Application Data

(60) Provisional application No. 62/940,484, filed on Nov. 26, 2019.

(51) Int. Cl.
*A61B 90/00* (2016.01)
*A61B 5/00* (2006.01)
(Continued)

(52) U.S. Cl.
CPC ............ *A61B 90/39* (2016.02); *A61B 5/0071* (2013.01); *A61B 8/481* (2013.01);
(Continued)

(58) Field of Classification Search
CPC ............ A61B 8/481; A61B 2090/3908; A61B 2090/3941
See application file for complete search history.

(56) References Cited

U.S. PATENT DOCUMENTS

| | | | |
|---|---|---|---|
| 6,356,782 B1 * | 3/2002 | Sirimanne | A61B 90/39 600/431 |
| 2010/0030072 A1 * | 2/2010 | Casanova | A61B 90/39 600/431 |

(Continued)

*Primary Examiner* — Bill Thomson
*Assistant Examiner* — Aminah Asghar
(74) *Attorney, Agent, or Firm* — Maynard Nexsen PC; John P. Zimmer

(57) ABSTRACT

A tissue implantation device comprises a capsule; and a population of ultrasound-switchable fluorophores incorporated in the capsule. A method of imaging a tissue implantation device in a biological environment comprises disposing the tissue implantation device in a biological environment, the population of ultrasound-switchable fluorophores having a switching threshold in the biological environment; exposing the biological environment to an ultrasound beam to form an activation region within the biological environment; switching the ultrasound-switchable fluorophores in the activation region from an off state to an on state; exciting the ultrasound-switchable fluorophores in the activation region with a beam of electromagnetic radiation; and detecting light emitted by the ultrasound-switchable fluorophores.

8 Claims, 16 Drawing Sheets

(51) Int. Cl.
*A61B 8/08* (2006.01)
*A61K 49/00* (2006.01)
*A61K 49/22* (2006.01)

(52) U.S. Cl.
CPC ........ *A61K 49/0089* (2013.01); *A61K 49/223* (2013.01); *A61K 49/225* (2013.01); *A61B 2090/3908* (2016.02); *A61B 2090/3941* (2016.02); *A61B 2090/3954* (2016.02); *A61B 2090/3979* (2016.02)

(56) References Cited

U.S. PATENT DOCUMENTS

| 2015/0064241 | A1* | 3/2015 | Conrad | A61B 5/0071 |
| | | | | 424/451 |
| 2015/0309014 | A1* | 10/2015 | Yuan | A61B 5/0071 |
| | | | | 702/19 |
| 2017/0209601 | A1* | 7/2017 | Kumar | A61L 31/14 |
| 2018/0085184 | A1* | 3/2018 | Bolan | G01R 33/5601 |

* cited by examiner 1.2x5.7 mm 1.5x5 mm

1x5 mm

METHODS FOR SURGICAL GUIDANCE IN BREAST CANCER SURGERY AND LYMPH NODE DISSECTION USING TWO OR MORE IMPLANTATION DEVICES COMPRISING A CAPSULE AND A POPULATION OF ULTRASOUND-SWITCHABLE FLUOROPHORES INCORPORATED IN THE CAPSULE

RELATED APPLICATION DATA

The present application claims priority pursuant to 35 U.S.C. § 119(e) to U.S. Provisional Patent Application Ser. No. 62/940,484 filed Nov. 26, 2019, which is incorporated herein by reference in its entirety.

STATEMENT REGARDING GOVERNMENT FUNDING

This invention was made with government support under contract CPRIT RP170564 awarded by Cancer Prevention Research Institute of Texas. The government may retain some rights to this invention.

FIELD

The invention is generally related to imaging markers, and, more specifically, to biopsy clips or localization seeds using ultrasound switchable fluorophores.

BACKGROUND

Approximately 1.7 million new cases of breast cancer are diagnosed globally each year, with almost 260,000 per year in USA alone. As a part of the treatment, most patients experience some type of surgery to remove tumors to avoid continuous growth and metastasis. When lymph nodes are suspected with metastasis, often sentinel and some or all axillary lymph nodes need to be dissected.

Typically tissue biopsies are performed on the breast tissue to obtain tissue samples at various locations. Tiny radiopaque clips/markers are routinely implanted during breast biopsy at each of the locations in the tissue where a tissue sample was removed. These clips serve as biopsy locational markers correlating a tissue sample with a specific location in the tissue, and serve as a locational guide for future procedures.

Approximately 30-50% of breast tumors requiring surgery are non-palpable. Unfortunately, current technologies for assisting physicians in localize these tumors during the actual time of surgery cannot be combined with the biopsy clips, since imaging of the clips is not possible during the time of surgery, being limited to pre-surgery. Consequently, current surgical approaches are unable to use the biopsy clips in real time to help delineate a tumor's boundary. Physicians need a device to intra-operatively locate these non-palpable tumors for removal during the surgery itself.

There are several standard localization techniques currently used to locate non-palpable tumors during surgery, including wire localization (WL), radioactive-seed localization (RSL), intra-operative ultrasound (IOUS), radiofrequency-seed localization (RF-SL, such as SAVIScout®), magnetic seed localization (MSL), photoacoustic seed localization (PA-SL), among others. Unfortunately, all of these localization techniques are not compatible with the clipping procedure in biopsy, because the implanted wire or seed used in these techniques cannot be left in situ for long term use. The implanted wire or seed must be surgically removed. In contrast, the biopsy requires the clips to remain in situ for long periods of time if the lesion is benign. Thus, patients have to experience similar painful procedures at least twice.

The standard localization techniques also have a number of additional drawbacks and disadvantages. For instance, all of the localization techniques have extremely low resolution (e.g. ~2-3 cm). Delineation of a tumor's boundary (even a non-palpable lesion) is highly desired and often critical for a surgeon to accurately remove a tumor and maximally preserve normal tissue. However, the poor resolution of current existing technologies cannot achieve this goal accurately. Additionally, each of the individual localization techniques has its own unique disadvantages. For instance, WL is invasive, stressful for patients, and it has to be done on the same day as the surgery. RSL generates radioisotope dependent-logistical and handling issues, the localization accuracy is limited when multiple seeds exist, and the number of the implanted seeds are limited and highly regulated due to safety issues related to radioactivity (≤3 per breast). IOUS is limited in its effectiveness due to the fact that many lesions cannot be seen from ultrasound because tumor physiology is similar enough to background tissue to make resolving the tumor tissue difficult. While contrast enhanced markers (such as haematoma) can be used to improve IOUS, signal degradation is still a major challenge. Techniques such as MSL, RF-SL and PA-SL require expensive seeds (~$450-$600 per seed), detection systems (~$100 k) or both, large seed size (RF-SL seeds are nearly 12 mm in length), and all are not suitable for tumor boundary delineation and multiple tumors localization due to no or very low spatial resolution between the seeds.

Breast conserving surgery (BCS) requires enough cancer-free margins of the resected specimen for avoiding cancer recurrence, while also requiring maximal preservation of normal breast tissue to give the best cosmetic outcome. An intraoperative imaging technique using a handheld imager that can accurately visualize tumor boundary and distinguish tumor tissue from background tissue is highly desirable. Unfortunately, such a technique and imager is not available or provided by the standard localization techniques currently available.

Pre-operative diagnostic imaging methods (MRI, CT, Ultrasound, etc.) are over limited utility for identify tumor boundary during surgery, because motion and deformation of soft breast tissue at different postures dramatically shift the breast tissue location. This makes co-registration of these pre-operative images with patient's anatomic structure extremely difficult, if not impossible, to perform during the surgery itself. Attempts to use WL and RSL to bracket a tumor for this purpose have been made, but the problems are obvious. Inserting multiple wires can cause more stresses and logistical problems, and the maximum number of implanted radioactive seeds per breast is strictly regulated (≤3) due to the safety issue. More critically, the spatial resolution is very low (~2-3 cm). Therefore, this bracketing method is only for very large tumors (>3 cm) and has shown limited clinical success.

Axillary lymph node metastases is a commonly observed in breast cancer patients, often resulting in axillary lymph node dissection (ALND) to remove the affected lymph nodes. However, ALND is a very aggressive approach, and has high morbidity, because it removes all or majority of axillary lymph nodes (~10-40 nodes). Considerable interest exists in avoiding ALND for qualified patients. Compared with ALND, targeted axillary dissection (TAD) selectively removes biopsy-confirmed metastasized axillary lymph nodes rather than wholesale removal of nearly all of the axillary lymph nodes. TAD has been found a better option for patients who have a pathologic complete response (pCR) to neoadjuvant therapy. Unfortunately, the limitation of TAD is a lack of an efficient and accurate method to identify and localize these targeted multiple lymph nodes for assessing treatment, to identify pCR patients, and to assure surgical removal of all the targeted nodes. Studies have shown that a large amount of patients (40-75%) have a pathologic complete response (pCR) to neoadjuvant chemotherapy, which provides opportunities to avoid ALND. Studies have also shown TAD is a reliable method (as low as 2% false-negative rate) for identifying pCR patients. Unfortunately, applying the above described standard breast lesion localization techniques for identification and localization of the targeted axillary lymph nodes brings many challenges. For instance multiple lymph nodes are frequently involved (~45% patients have ≥3 targeted nodes) and the seeds need stay in the nodes for a few months due to the lengthy neoadjuvant chemotherapy. The disadvantages and limitations of the standard localization techniques for TAD have been well discussed in literature. To facilitate TAD, an ideal technique should be comfortable for patients, easy to perform, and the procedures should not entail radioactivity. An ideal technique will allow clips/seeds to be placed in targeted nodes during the biopsy, where the clips/seeds can remain in the nodes for long periods of time while also functioning as real-time locational marker during the surgery itself. Such a technique would eliminate the need for a second invasive procedure to place a locational marker, while still providing identification of affected lymph nodes.

SUMMARY

In one aspect, a tissue implantation device comprises a capsule; and a population of ultrasound-switchable fluorophores incorporated in the capsule. The tissue implantation device can comprise a biopsy clip or a localization seed in some embodiments.

The capsule can comprise an ultrasound energy absorbing material having a higher acoustic-to-thermal conversion efficiency than soft tissue. For example, in some cases the ultrasound energy absorbing material comprises silicone. In some embodiments, a population of ultrasound-switchable fluorophores is dispersed throughout the ultrasound energy absorbing material.

In some embodiment, the capsule comprises an outer shell that at least partially defines a central receiving space. The outer shell can comprise a contrast agent in some cases, where the contrast agent comprises a metal, a metal particle, a metal mesh, a gas, or gas bubbles. In some instances, the contrast agent is positioned in the central receiving space or in both the outer shell and in the central receiving space. In some embodiments, the capsule further comprises one or more gas-containing compartments. The gas-containing compartments can comprise a gas contrast agent.

In some cases, after injection the capsule may thermally expanded slightly due to its material has a large thermal expansion coefficient and the temperature difference between the living biological tissue (such as ~36-37° C.) and the environment (such as room temperature ~18-23° C.), which can help fix the capsule in the soft tissue. In some cases, the outer shell of the capsule comprises two or more immobilizers positioned on an outer surface of the outer shell. After capsule insertion into soft tissue, the immobilizers can engage with the soft tissue to fix the capsule in the soft tissue, and can prevent migration of the capsule in the soft tissue in some cases.

In some instances, the population of ultrasound-switchable fluorophores are positioned in the central receiving space. In other cases, the population of ultrasound-switchable fluorophores are dispersed in the outer shell. The ultrasound-switchable fluorophores can comprise a thermosensitive polymer. Exemplary thermo-sensitive polymers comprise dipalmitoyl-sn-glycero-3-phosphocholine (DPPC), poly-N-isopropylacrylamide (PNIPAM), a pluronic, or polyethylene glycol (PEG). In some cases, the thermos-sensitive polymer comprises a copolymer of N-isopropylacrylamide with one or more of acrylamide, N-tert-butylacrylamide, acrylic acid, an allylamine, or a polyoxypropylene-polyoxyethylene block copolymer. The ultrasound-switchable fluorophores can comprise or further comprise a fluorescent material having a peak emission wavelength in the red, near infrared or infrared spectrum in some embodiments.

In another aspect, a method of imaging a tissue implantation device in a biological environment comprises: disposing a tissue implantation device described herein in a biological environment, the population of ultrasound-switchable fluorophores having a switching threshold in the biological environment; exposing the biological environment to an ultrasound beam to form an activation region within the biological environment; switching the fluorophores within the activation region from an off state to an on state; exciting the ultrasound-switchable fluorophores in the activation region with a beam of electromagnetic radiation; and detecting light emitted by the ultrasound-switchable fluorophores. In some embodiments, the method further comprising correlating a size, shape, position, orientation, or any combination thereof, of the tissue implantation device in the biological environment based on the detected light emitted by the ultrasound-switchable fluorophores.

In some cases, exposing the biological environment to an ultrasound beam comprises scanning the biological environment with the ultrasound beam. In some instances, the beam of electromagnetic radiation is in the red or near-infrared region (NIR) of the electromagnetic spectrum. Light emitted by the ultrasound-switchable fluorophores can have a peak emission wavelength in the red or near-infrared region (NIR) or infrared spectrum in some cases.

In some embodiments, the ultrasound-switchable fluorophores in the activation region are excited by a single beam of electromagnetic radiation.

In some instances, the tissue implantation device is disposed at a depth of 0.1-10 centimeters (cm) below a surface of the biological environment. The biological environment can comprise a tumor, tumor boundary, and normal tissue, including vasculature. In some embodiments, the biological environment includes breast, prostate, head, neck, throat, mouth, thyroid, skin, colon, cervix, vascular, or uterine tissue.

Disposing the tissue implantation device in the biological environment can in some cases further comprise disposing two or more tissue implantation devices in the biological environmental, and resolving the two or more tissue implantation devices by detecting the light emitted by the ultrasound-switchable fluorophores. The two or more tissue implantation devices can comprise the same or different ultrasound-switchable fluorophores having the same or different peak emission wavelengths. In some cases, the different peak emission wavelengths have average peak emission wavelengths separated by 25-75 nm. Moreover, in some cases, the two or more tissue implantation devices comprise different ultrasound-switchable fluorophores having the same or different switching thresholds.

DETAILED DESCRIPTION

Figure 1A:
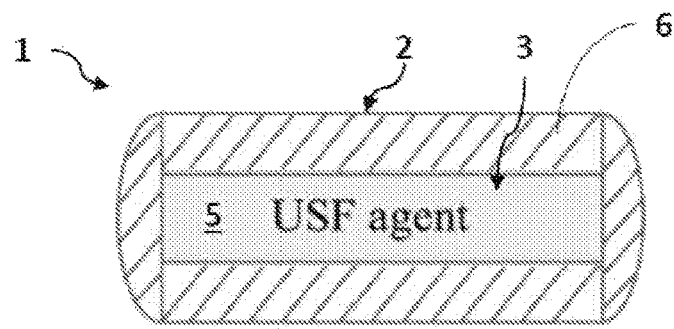
FIGS. 1A-1H are cross-sectional views of different embodiments of a tissue implantation device.

Embodiments described herein can be understood more readily by reference to the following detailed description, examples, and figures (referred to as "FIGS."). Elements, apparatus, and methods described herein, however, are not limited to the specific embodiments presented in the detailed description, examples, and figures. It should be recognized that the exemplary embodiments herein are merely illustrative of the principles of the invention. Numerous modifications and adaptations will be readily apparent to those of skill in the art without departing from the spirit and scope of the invention.

In addition, all ranges disclosed herein are to be understood to encompass any and all subranges subsumed therein. For example, a stated range of "1.0 to 10.0" should be considered to include any and all subranges beginning with a minimum value of 1.0 or more and ending with a maximum value of 10.0 or less, e.g., 1.0 to 5.3, or 4.7 to 10.0, or 3.6 to 7.9.

All ranges disclosed herein are also to be considered to include the end points of the range, unless expressly stated otherwise. For example, a range of "between 5 and 10" or "5 to 10" or "5-10" should generally be considered to include the end points 5 and 10.

Further, when the phrase "up to" is used in connection with an amount or quantity; it is to be understood that the amount is at least a detectable amount or quantity. For example, a material present in an amount "up to" a specified amount can be present from a detectable amount and up to and including the specified amount.

Additionally, in any disclosed embodiment, the terms "substantially," "approximately," and "about" may be substituted with "within [a percentage] of" what is specified, where the percentage includes 0.1, 1, 5, and 10 percent.

As previously discussed, during tissue biopsy or tumor localization, tiny clips or localization seeds are often implanted at the biopsy or tumor site, and serve as locational markers. Conventional clips and seeds are only resolvable using large and complicated imaging devices, such as a x-ray imager or computed tomography (CT) scanner, or poorly resolvable detection techniques. Described herein is a tissue implantation device that can, in some embodiments, provide one or more advantages compared to conventional biopsy clips or localization seeds. In some cases, the tissue implantation device is a biopsy clip or localization seed that uses ultrasound-switchable florescence (USF). Such devices and methods described herein can provide various advantages, as compared to other biopsy clips, localization seeds, and/or imaging methods, including other USF imaging methods.

I. Tissue Implantation Devices

In an aspect, a tissue implantation device is described herein. The tissue implantation device is a biopsy clip or a localization seed in some cases. The tissue implantation device comprises a capsule; and a population of ultrasound-switchable fluorophores incorporated in the capsule. For purposes described herein, ultrasound-switchable fluorophores may generally also be referred to as "USF" or "USF agents" for purposes of brevity.

The capsule can have any shape not inconsistent with the objectives of this disclosure. Such shapes include rods, cylinders, corks, helical coils, letters, ribbons, hearts, buckles, wings, and the like. The shape of the capsule can vary and be customized into any unique shape to provide better visualization and differentiation under x-ray, and to reduce the possibility of potential migration The length of the capsule can be anywhere from 1-15 mm, depending on the application. Exemplary lengths can include 1-5 mm, 2-5 mm, 3-5 mm, 1-10 mm, 2-8 mm, 3-6 mm, 5-15 mm, 7-15 mm, 10-15 mm, 12-15 mm, 5-12 mm, 5-10 mm, 5-8 mm, 1 mm, 2 mm, 3 mm, 4 mm, 5 mm, 6 mm, 7 mm, 8 mm, 9 mm, 10 mm, 11 mm, 12 mm, 13 mm, 14 mm, or 15 mm. The diameter or width of the capsule can be between 0.1-3 mm, 0.1-2 mm, 0.1 mm, 0.25 mm, 0.5 mm, 0.75 mm, 1 mm, 1.25 mm, 1.5 mm, 1.75 mm, or 2 mm.

The capsule can be made from an ultrasound energy absorbing material having a higher acoustic-to-thermal conversion efficiency than soft tissue. Exemplary embodiments of an ultrasound energy absorbing material include silicone, a polyurethane, polydimethylsiloxane (PDMS), various polymer-gels, combinations of different materials, or any other ultrasound energy absorbing material not inconsistent with the objectives of this disclosure. FIGS. 1A-2C illustrate different tissue implantation device 1 embodiments having a capsule 2. The capsule can be made using any method not inconsistent with the objectives of this disclosure. For instance, the capsule can be made using 3D printing, injection molding, casting, and the like.

Figure 1B:
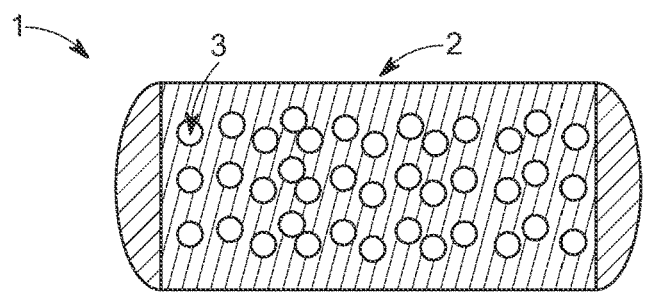

In some embodiments, the population of ultrasound-switchable fluorophores are dispersed throughout the ultrasound energy absorbing material, such as is illustrated in the embodiment shown in FIG. 1B.

In some cases, the capsule comprises an outer shell that at least partially defines a central receiving space. FIGS. 1A and 1C-2C show exemplary capsules 1 having an outer shell 6 that at least partially defines a central receiving space 5. In some embodiments, the population of ultrasound-switchable fluorophores 3 are positioned in the central receiving space, as shown for example in FIGS. 1A, 1C, 1E, and 1G-2C. In other embodiments, the population of ultrasound-switchable fluorophores 3 are dispersed in the outer shell 6, as illustrated in FIGS. 1D and 1F.

Any ultrasound-switchable fluorophore or combination of differing ultrasound-switchable fluorophores not inconsistent with the objectives of the current disclosure may be used. An "ultrasound-switchable" fluorophore, for reference purposes herein, comprises a fluorophore operable to switch between an on state and an off state in response to exposure to an ultrasound beam. The ultrasound beam can be either directly or indirectly responsible for the switching response of the fluorophore. For example, in some cases, the ultrasound beam interacts directly with the fluorophore, resulting in a switch between fluorescence states of the fluorophore. In other cases, the ultrasound beam interacts directly with the immediate environment or microenvironment of the fluorophore and changes at least one property of the fluorophore's microenvironment. In such cases, the fluorophore can switch between on and off fluorescence states in response to the environmental change induced by the ultrasound beam. A non-limiting example of an environmental change would be a change in temperature. Thus, the fluorophore can be indirectly switchable in response to exposure to an ultrasound beam.

The "on" state of a fluorophore, for reference purposes herein, comprises either (1) a state at which the fluorescence intensity of the fluorophore is relatively high compared to the "off" state of the fluorophore, at which the fluorescence intensity is relatively low (assuming the fluorophore is similarly excited in both the on state and the off state); or (2) a state at which the fluorescence lifetime of the fluorophore is relatively long compared to the "off" state of the fluorophore, at which the fluorescence lifetime is relatively short (again assuming the fluorophore is similarly excited). Further, in both cases, the on and off states substantially define a step function in the fluorescence intensity or lifetime profile when plotted as a function of a critical switching parameter such as temperature. A fluorophore having a longer lifetime in an on state than an off state can be particularly suitable for use in methods described herein using time-gated or time-delayed detection of emitted photons from fluorophores, such as time-gated detection in which only those photons received after a relatively long delay following excitation are counted by the detector as part of the USF signal. In some cases, the on state of a fluorophore exhibits at least about 70 percent, at least about 80 percent, or at least about 90 percent of the theoretical maximum fluorescence intensity of the fluorophore, and the off state of the fluorophore exhibits no more than about 50 percent, no more than about 30 percent, no more than about 10 percent, or no more than about 5 percent of the theoretical maximum fluorescence intensity of the fluorophore.

The physical cause for the existence of an on state versus an off state can vary. For example, in some cases, the fluorescence intensity or fluorescence lifetime of a fluorophore changes dues to a conformational or chemical change of the fluorophore in response to a change in environmental conditions, such as exhibited by some thermoresponsive polymers, pH-sensitive chemical species, or pressure sensitive materials. In some cases, the fluorescence intensity or fluorescence lifetime of a fluorophore changes in response to internal fluorescence quenching, wherein such quenching can be directly or indirectly induced by the presence of ultrasound.

For example, in some embodiments, a fluorophore described herein comprises a Förster resonance energy transfer (FRET) donor species and a FRET acceptor species, and the distance between the FRET donor species and the FRET acceptor species is altered by the presence of an ultrasound beam. The FRET donor species can be a first fluorescent species or other chromophore, and the FRET acceptor species can be a second fluorescent species or other chromophore. In such cases, as understood by one of ordinary skill in the art, FRET energy transfer between the donor species and the acceptor species can result in quenching of the fluorescence of the donor species. Thus, the acceptor species can be considered to be a fluorescence quenching species of the fluorophore. Any donor-acceptor pair not inconsistent with the objectives of the current disclosure may be used in FRET-based fluorophores described herein. For example, in some cases, the donor species comprises Alexa Fluor 546 and the acceptor species comprise Alexa Fluor 647. Other combinations of acceptor species and donor species are also possible.

In some embodiments, a fluorophore described herein comprises a microbubble comprising one or more FRET donor species and one or more FRET acceptor species attached to the exterior surface of the microbubble, wherein the microbubble is operable to change in size in response to the presence of an ultrasound beam. The change in size can increase or decrease the distance between the FRET donor species and the FRET acceptor species, thus reducing or increasing the FRET energy transfer efficiency. As a result, the fluorescence quenching and the overall fluorescence intensity of the microbubble can vary based on the size of the microbubble. In some embodiments, the microbubbles are positioned in the central receiving space of the tissue implantation device.

A microbubble described herein can have any size and be formed of any chemical species not inconsistent with the objectives of the current invention. In some cases, a microbubble has a diameter between about 1 μm and about 10 μm or between about 1 μm and about 5 μm. Other sizes of microbubbles may also be used. Moreover, in some embodiments, a microbubble described herein comprises a gas core surrounded by a shell formed from a polymeric material, such an organic polymeric material. In other cases, the shell is formed from a lipid material. In some embodiments, a microbubble comprises a shell formed from one or more of albumin, galactose, lipid, and sulfur hexafluoride. In addition, the gas core of a microbubble described herein can comprise one or more of air, nitrogen, and a perfluorocarbon such as octafluoropropane. Moreover, in some cases, a microbubble described herein is formed from a commercially available microbubble, such as a SonoVue™, Optison™, Imagent™, Definity™, or Targestar™ microbubble. A FRET donor and/or acceptor species described herein can be attached to the surface of such a microbubble in any manner not inconsistent with the objectives of the current invention. In some cases, for instance, a donor and/or acceptor species is attached to the exterior surface of a commercially available microbubble using one or more of a carbodiimide, maleimide, or biotin-streptavidin coupling scheme. Moreover, any other coupling scheme not inconsistent with the objectives of the current disclosure can be used to attach a donor and/or acceptor species to a microbubble.

In an embodiment, gas-filled micro-particles, such as the above described microbubbles, generate a short but high temperature pulse in and around the particle surface when the microbubble is irradiated with an ultrasound pulse at diagnostic intensity level. This short temperature pulse spatially decays very fast (only ~0.2° C. left at a distance of 1 micron away from the bubble surface). In ultrasound imaging, tissue overheating caused by microbubbles is minimalized from this fast temperature decay. However, this microscopic heating principle is effective for heating ultrasound switchable fluorophores, because ultrasound switchable fluorophores are small nanoparticles that can be attached on the microbubble's surface. The, ultrasound switchable fluorophores (e.g. USF Contrast Agents) can be attached to a microbubble via a biotin/streptavidin linkage. Moreover, any other linkage not inconsistent with the objectives of the current disclosure can be used to attach ultrasound switchable fluorophores to a microbubble.

In other embodiments, a highly ultrasound-absorbing polymer, biodegradable polyurethane with pendent carboxyl groups (PU—COOH), can alternatively be used instead of the microbubbles. These ultrasound-absorbing polyurethanes make relatively rigid gas-filled sub-micro-particles (~700 nm in diameter). For example, in some embodiments, the ultrasound-absorbing polymer can comprise a Pluronic polymer with pendent carboxyl groups similar in size to the polyurethanes, such as F127, F98, F98-PEG20k, F98-PEG30k, F98-PEG40k, F68 and its PEGylated polymers, which have been functionalized to incorporate pendent carboxyl groups. These ultrasound-absorbing polymers are generally smaller in diameter compared to microbubbles, reducing their acoustic attenuation compared to microbubbles. However, their relatively rigid structures can sometimes display more resilient bio-stability than microbubbles, and can, in some embodiments, be distributed in a capsule material, such as silicone, polyurethane, or the like. Similar to the microbubbles, biotin can be incorporated onto the surface of the ultrasound-absorbing polymers, and the USF contrast agents can be attached using the streptavidin linkage. Moreover, any other coupling scheme not inconsistent with the objectives of this disclosure can be used to attach a donor and/or acceptor species to a highly ultrasound-absorbing polymer.

In some embodiments, a fluorophore described herein comprises a thermoresponsive/thermos-sensitive polymer. A "thermoresponsive" polymer, for reference purposes herein, comprises a polymer having a physical or chemical property that changes in a temperature-dependent manner, wherein the change is a discontinuous or binary change. For example, in some cases, the physical conformation or polarity of a thermoresponsive polymer changes in a temperature-dependent manner, and the thermoresponsive polymer exhibits a first conformation below a threshold temperature and a second, substantially different conformation above the threshold temperature. In some embodiments, for instance, a thermoresponsive polymer exhibits an expanded coil or chain confirmation below a threshold temperature and exhibits a compact or globular conformation above the threshold temperature. In some such cases, the threshold temperature can be referred to as the "lower critical solution temperature" (LCST) of the polymer.

Any thermoresponsive/thermo-sensitive polymer not inconsistent with the objectives of the current invention may be used. In some embodiments, a thermoresponsive polymer comprises dipalmitoyl-sn-glycero-3-phosphocholine (DPPC), a poly(N-isopropylacrylamide) (PNIPAM), a pluronic, a polyethylene glycol (PEG), or a copolymer of N-isopropylacrylamide with one or more of acrylamide, N-tert-butylacrylamide, acrylic acid, allylamine, or a polyoxypropylene-polyoxyethylene block copolymer. In other cases, a thermoresponsive polymer comprises a poly(N-vinylcaprolacatam) (PVCL) or a poloxamer such as a Pluronic polymer. Other thermoresponsive polymers may also be used.

Additionally, in some cases, a thermoresponsive polymer of a fluorophore described herein comprises one or more fluorescent moieties or is conjugated to one or more fluorescent species, such as one or more fluorescent dye molecules. The fluorescent dye molecules can comprise any fluorescent dyes not inconsistent with the objectives of this disclosure, such as the commercially available ZnPC (Zinc phthalocyanines) family of dyes (e.g. ZnPc, ZnPcTTB, ZnPcHF, ZnPcOB, among others), the $ADP(CA)_2$ family of dyes, or ICG-based agents (indocyanine greens, including ICG-encapsulated agents such as ICG-encapsulated poly(N-isopropylacrylamide) (PNIPAM)). The thermoresponsive polymer can be conjugated to the fluorescent species in any manner not inconsistent with the objectives of the current invention. For example, in some cases, a thermoresponsive polymer is coupled to a fluorescent species through one or more covalent bonds such as one or more ester bonds or one or more amide bonds.

Some non-limiting examples of an ultrasound-switched fluorescence process using a thermoresponsive fluorophore are illustrated in U.S. Patent Application Publication No. 2015/0309014 to Yuan et al. (hereinafter "the '014 publication"), which is incorporated herein in its entirety. As described in the '014 publication, a thermoresponsive polymer can be conjugated to a fluorescent species to provide a fluorophore. The fluorophore has a chain conformation and a globular conformation described hereinabove, and the conformation is temperature-dependent. Further, the transition from one conformation to the other results in a change in the fluorescence intensity or lifetime of the fluorescent species. As described further herein, the change in fluorescence intensity or lifetime can be due to differences in the microenvironment of the fluorescent species when the polymer is in the chain conformation compared to the globular conformation. For example, in some cases, the polarity and/or viscosity of the polymer environment experienced by the fluorophore changes depending on whether the polymer is in the chain conformation or the globular conformation.

Further, in some embodiments, a fluorophore described herein comprises a fluorescent material dispersed in and/or attached to the surface of a thermoresponsive polymer nanoparticle. Moreover, the fluorescence properties of the fluorescent material can be dependent on a change of the conformation, polarity, or other physical or chemical property of the polymer nanoparticle. In addition, the property change can be a temperature-dependent change. In this manner, a change in temperature of the thermoresponsive polymer nanoparticle can result in a change in fluorescence intensity and/or lifetime of the fluorescent material, including a change between an on state of the fluorescent material and an off state of the fluorescent material.

For example, in some embodiments, a thermoresponsive polymer nanoparticle can exhibit a temperature-dependent polarity, and the fluorescent material dispersed in the nanoparticle can exhibit a polarity-dependent fluorescence intensity and/or lifetime. Thus, a change in the temperature of the nanoparticle can result in a change in the fluorescence intensity and/or lifetime of the fluorophore.

In another exemplary embodiment, a thermoresponsive polymer nanoparticle can have a hydrophilic interior below a threshold temperature and a hydrophobic interior above the threshold temperature. Thus, such a nanoparticle can exhibit a temperature-dependent size when dispersed in a polar or non-polar solvent. For example, when dispersed in water or another polar solvent below the threshold temperature, the nanoparticle can exhibit a larger size due to the presence of water in the hydrophilic interior of the nanoparticle. Similarly, above the threshold temperature, the nanoparticle can exhibit a smaller size due to the exclusion of water from the now hydrophobic interior of the nanoparticle. In this manner, a fluorescent material dispersed in the nanoparticle can have a temperature-dependent concentration, which can result in temperature-dependent fluorescence properties of the overall fluorophore. This process is illustrated schematically in the '014 publication, specifically in FIG. 2. Additionally, in some embodiments, the thermosensitive polymer nanoparticle can be positioned in the central receiving space of the tissue implantation device, embedded within the capsule material itself, or be in both the central receiving space and the capsule material.

In another embodiment, an ultrasound-switchable fluorophore is formed by incorporating a fluorescent material such as a fluorescent dye within the interior of a polymeric nanoparticle or micelle, such that the polymeric nanoparticle or micelle acts as a nanocapsule for the fluorescent material. Moreover, the polymeric nanoparticle can be formed from a thermoresponsive polymer, such as a thermoresponsive polymer described hereinabove. Non-limiting examples of polymers suitable for forming nanocapsules described herein include Pluronic F127, F98, F98-PEG20k, F98-PEG30k, F98-PEG40k, F68 and its PEGylated polymers, poly(N-isopropylacrylamide) or a copolymer of N-isopropylacrylamide with one or more of acrylamide, N-tert-butylacrylamide, acrylic acid, allylamine, or a polyoxypropylene-polyoxyethylene block copolymer, or poly(N-vinylcaprolacatam) (PVCL). Moreover, in some instances, a nanoparticle or nanocapsule can be formed by copolymerizing a thermoresponsive polymer described hereinabove with a polyethylene glycol (PEG) and/or by conjugating a PEG as a pendant group to a thermoresponsive polymer. Such a fluorophore, in some cases, can have a switching threshold that is controlled at least in part by the inclusion of PEG, as described further in the '014 publication.

A polymer nanoparticle such as a thermoresponsive polymer nanoparticle or a polymer nanocapsule described herein can have any size or shape not inconsistent with the objectives of the current disclosure. In some embodiments, for instance, a thermoresponsive polymer nanoparticle is substantially spherical and has a diameter between about 10 nm and about 300 nm, between about 50 nm and about 250 nm, between about 50 nm and about 200 nm, or between about 70 nm and about 150 nm. In some cases, a polymer nanocapsule is substantially spherical and has a diameter of less than about 100 nm or less than about 50 nm. In some instances, a polymer nanocapsule has a size between about 20 nm and about 90 nm, between about 20 nm and about 80 nm, or between about 20 nm and about 70 nm. Other sizes and shapes are also possible.

Further, any fluorescent material not inconsistent with the objectives of the current invention may be dispersed in and/or attached to a thermoresponsive polymer nanoparticle or other polymer nanoparticle to form a fluorophore described herein. In some embodiments, as described herein, the fluorescent material exhibits a polarity-sensitive fluorescence intensity and/or lifetime. In other cases, the fluorescent material exhibits a temperature-dependent, viscosity-dependent, pH-dependent, and/or an ionic strength-dependent fluorescence intensity and/or lifetime.

Non-limiting examples of fluorescent materials suitable for use in some embodiments described herein include organic dyes such as N,N-dimethyl-4-benzofurazansulfonamide (DBD); 4-(N,N-dimethylaminosulfonyl)-7-(2-aminoethylamino)-2,1,3-benzoxadiazole (DBD-ED); indocyanine green (ICG); a Dylight-700 such as Dylite-700-2B; IR-820; 3,3'-Diethylthiatricarbocyanine iodide (DTTCI); LS-277; LS-288; a cypate; a rhodamine dye such as rhodamine 6G or rhodamine B; or a coumarin. In some instances, a fluorescent material comprises an azadipyrromethene. In addition, in some cases, a fluorescent material comprises an inorganic species such as a semiconductor nanocrystal or quantum dot, including a II-VI semiconductor nanocrystal such as ZnS or CdSe or a III-V semiconductor nanocrystal such as InP or InAs. In other instances, a fluorescent material comprises a Lanthanide species. Additional non-limiting examples of fluorescent materials suitable for use in an ultrasound-switchable fluorophore described herein include the fluorescent materials described in Amin et al., "Syntheses, Electrochemistry, and Photodynamics of Ferrocene-Azadipyrromethane Donor-Acceptor Dyads and Triads," *J. Phys. Chem. A* 2011, 115, 9810-9819; Bandi et al., "A Broad-Band Capturing and Emitting Molecular Triad: Synthesis and Photochemistry," *Chem. Commun.*, 2013, 49, 2867-2869; Jokic et al., "Highly Photostable Near-Infrared Fluorescent pH Indicators and Sensors Based on BF2-Chelated Tetraarylazadipyrromethane Dyes," *Anal. Chem.* 2012, 84, 6723-6730; Jiang et al., "A Selective Fluorescent Turn-On NIR Probe for Cysteine," *Org. Biomol. Chem.*, 2012, 10, 1966-1968; and Kucukoz et al., "Synthesis, Optical Properties and Ultrafast Dynamics of Aza-boron-dipyrromethane Compounds Containing Methoxy and Hydroxy Groups and Two-Photon Absorption Cross-Section," *Journal of Photochemistry and Photobiology A: Chemistry* 247 (2012), 24-29; the entireties of which are hereby incorporated by reference. Other fluorescent materials may also be used.

An ultrasound-switchable fluorophore described herein can have any fluorescence emission profile not inconsistent with the objectives of the current invention. For example, in some embodiments, a fluorophore exhibits an emission profile including visible light or centered in the visible region of the electromagnetic spectrum, such as between 450 nm and 750 nm, 500 nm and 700 nm, or 550 nm and 650 nm. In some cases, a fluorophore exhibits an emission profile including red light, infrared (IR) light, or light centered in the IR region of the electromagnetic spectrum. For example, in some instances, a fluorophore described herein exhibits an emission profile centered in the near-IR (NIR, 750 nm-1.4 μm), short-wavelength IR (SWIR, 1.4-3 μm), mid-wavelength IR (MWIR, 3-8 μm), or long-wavelength IR (LWIR, 8-15 μm). Moreover, in some embodiments, a fluorophore described herein has an emission profile overlapping with a wavelength at which water and/or biological tissue has an absorption minimum, such as a wavelength between about 700 nm and about 800 nm, about 800 nm and about 900 nm, about 900 nm and 1.1 μm, or between about 1.25 μm and about 1.35 μm. Additionally, in some cases, a population of ultrasound-switchable fluorophores described herein comprise fluorophores having differing emission profiles for purposes of multiplexed imaging. For example, in some cases, a first fluorophore of a population can emit in the NIR and a second fluorophore of the population can emit in the visible region of the electromagnetic spectrum. In some instances, a fluorophore of the population has an emission spectra in one portion of the NIR, and the second fluorophore of a population has emission spectra in a different portion of the NIR, such as in the NIR-I and/or NIR-II regions (discussed in detail below).

In some embodiments, different populations of ultrasound-switchable fluorophores described herein comprise different fluorophores having different emission profiles for purposes of multiplexed imaging. For example, an emission profile of a first population of ultrasound switchable fluorophores having a first fluorophore can be between about 680 nm and about 710 nm, and the emission profile of a second population of ultrasound switchable fluorophores having a second fluorophore can be between about 740 nm and about 770 nm. In embodiments having a third population of ultrasound switchable fluorophores having a third fluorophore, the emission profile of a third fluorophore can be >840 nm or >900 nm. These emission profiles are merely exemplary, and in some instances the first, second, or third ultrasound-switchable fluorophores comprise a fluorescent material having a peak emission wavelength between 680 nm and 710 nm; between 740 nm and 770 nm, >800 nm, or >900 nm. In some instances, the first ultrasound-switchable fluorophores are configured to emit light having a first average peak wavelength and the second ultrasound-switchable fluorophores are configured to emit light having a second average peak wavelength, and wherein the second average peak wavelength is 25-75 nm longer than the first average peak wavelength. Moreover, this general principle can be applied to embodiments where n populations of ultrasound switchable fluorophores having n fluorophores are used. For example, a third ultra-sound switchable fluorophore can be configured to emit light having a third average peal wavelength that is 25 nm to 75 nm longer than the second average peak wavelength. In this manner, multiplexed imaging can be achieved. As described in more detail in Section II herein, two or more tissue implantation devices comprising different populations of ultrasound-switchable fluorophores can be used as biopsy clips or localization seeds to not only delineate tumor boundaries, but also can be used to encode tumor orientation using multiplexed imaging.

For safety purposes, conventional biopsy clips and localization seeds are commonly designed to be visualized by at least another modality, such as x-ray, ultrasound (US), or MM. In the event that the primary modality is unresolvable, the second modality functions as a backup.

In some instances, the material comprising the capsule itself functions as an image contrasting agent, with no other contrast agents/enhancers being present. Using silicone as an example, when the capsule is made from silicone, the silicone itself can generate an imaging contrast for x-ray, ultrasound, or MM imaging. Thus, while USF serves as the primary imaging method, the silicone serves as a secondary, back-up imaging method in the event that USF is unresolvable. FIGS. 1A and 1B illustrate different embodiments of this approach. In FIG. 1A, a USF agent 3 is positioned in a central receiving space 5 of the capsule. In FIG. 1B, the USF agent 3 is dispersed throughout the capsule 2, and the capsule 2 does not have a central receiving space 5.

In some embodiments, a tissue implantation device described herein can comprise a contrast agent. The contrast agent can be any contrast agent not inconsistent with the objectives of this disclosure. In some instances, the contrast agent comprises a metal, a metal particle, a metal mesh, a gas, or gas bubbles. In some instances, the contrast agent is positioned in the central receiving space, in the outer shell, or in both the outer shell and in the central receiving space of the capsule. In some embodiments, the capsule can comprise or further comprise one or more gas-containing compartments. The gas containing compartments can be a compartment within the central receiving space of the capsule, the central receiving space itself, or a gas bubble embedded within the material comprising the capsule itself. The gas-containing compartments can comprise a gas contrast agent. Exemplary metals comprise titanium, stainless steel, gold, silver, barium, alloys thereof. Additionally, non-metal contrast agent materials are also contemplated, these non-metal contrast agent materials being useful for enhancing x-ray contrast, such as iodine. Exemplary gas contrast agent comprise perfluorocarbon, sulfur hexafluoride, atmospheric air, nitrogen, and the like.

Figure 1C:
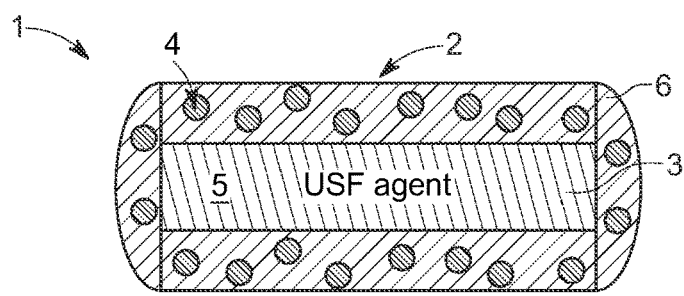
Figure 1D:
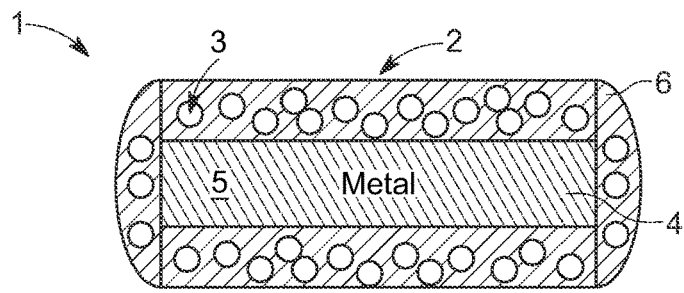
Figure 1E:
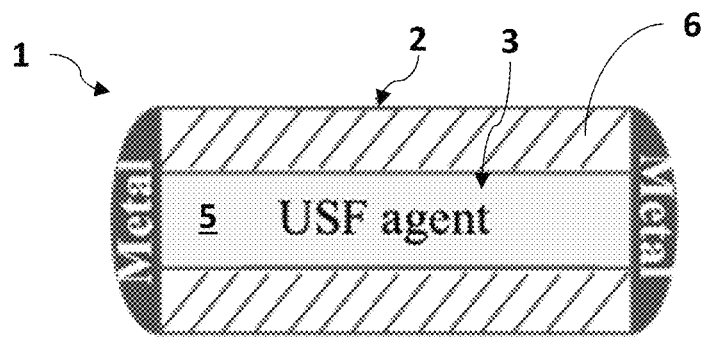
Figure 1F:
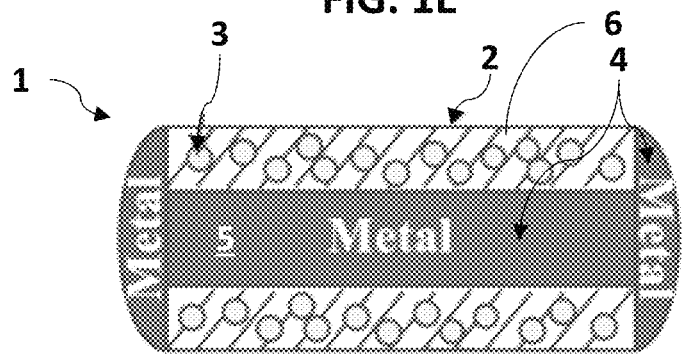
Figure 1G:
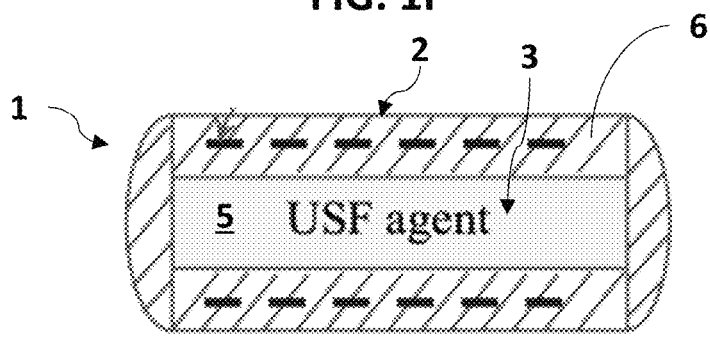
Figure 1H:
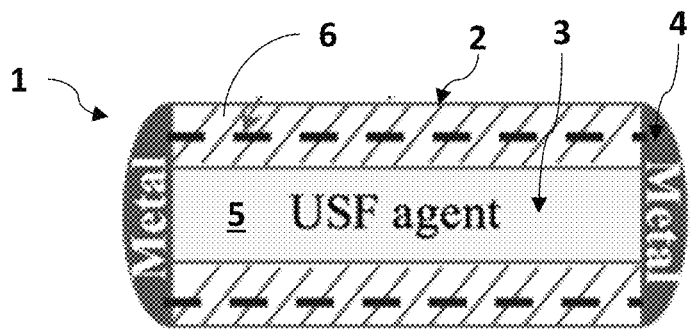
Figure 2A:
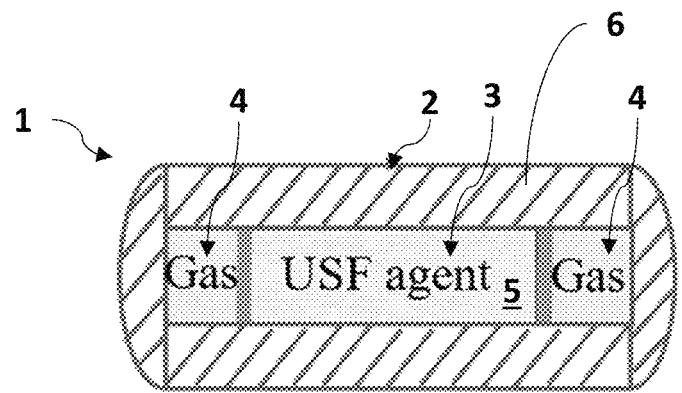
FIGS. 2A-2C are cross-sectional views of different embodiments of a tissue implantation device having a gas contrast agent.
Figure 2B:
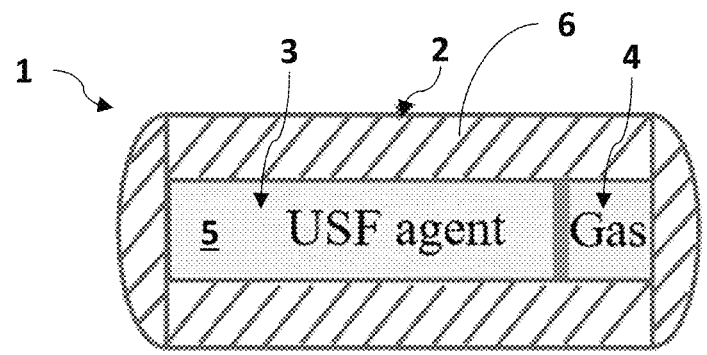
Figure 2C:
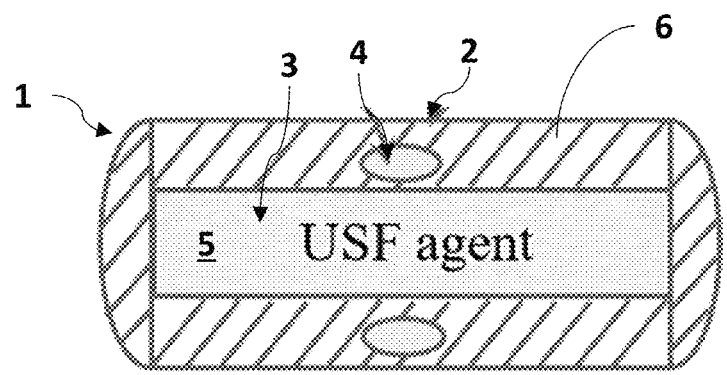

FIGS. 1C-2C illustrate various embodiments of tissue implantation devices 1 having a contrast agent 4 present in the capsule. As shown in FIGS. 1C-2C, exemplary contrast agents 4 can include metal contrast agents, metal mesh, gas compartments, and/or gas bubbles that increase the ultrasound reflection properties of device. FIG. 1C retains the same features as those in FIG. 1A, except that a contrast agent/enhancer 4 has been mixed into capsule material. In FIGS. 1D and 1F, a metal contrast agent 4 has been positioned into the central receiving spare 5, with the USF agent 3 being dispersed in the capsule material. In FIGS. 1E, 1F, and 1H, metal end caps are present on the capsule 2. In FIGS. 1G and 1H, a metal mesh 4 has been incorporated into the capsule material to serve as a contrast agent/enhancer. Typically, adding metal or metal mesh in the tissue implantation device 1 increases the x-ray absorption and ultrasound reflection of the device 1. In FIGS. 2A-2C, gas compartments or gas bubbles 4 are present in device 1, whether as one or more gas compartments within the central receiving space 5 (FIGS. 2A and 2B) or buried within the outer shell 6 of the capsule 2. Typically, the presence of a gas in capsule 2 increases ultrasound reflection properties of the device 1.

Conventional biopsy clips and localization seeds can pose an issue with migration within a tissue over time, greatly lowering their effectiveness as location markers. In some embodiments, material forming the capsule of tissue implantation devices described herein undergoes thermal expansion from room temperature (~20° C. before injection) to body temperature (~37° C. after injection). In some instances, a diameter of the tissue implantation device will increase 1-20%, 2-18%, 3-17%, 4-16%, 5-15%, 6-14%, 7-13%, 8-12%, 1-5%, 5-10%, 10-15%, 15-20%, 1%, 2%, 3%, 4%, 5%, 6%, 7%, 8%, 9%, 10%, 11%, 12%, 13%, 14%, 15%, 16%, 17%, 18%, 19%, or 20% upon thermal expansion after injection. Using silicone as an exemplary capsule material, silicone has a high thermal expansion coefficient of $275 \times 10^{-6}$/k, which is ~21 times higher than conventionally used metal seeds ($13 \times 10^{-6}$/k) In some cases, the thermal expansion fixes the tissue implantation device in the surrounding tissue and prevent device migration.

Figure 3:
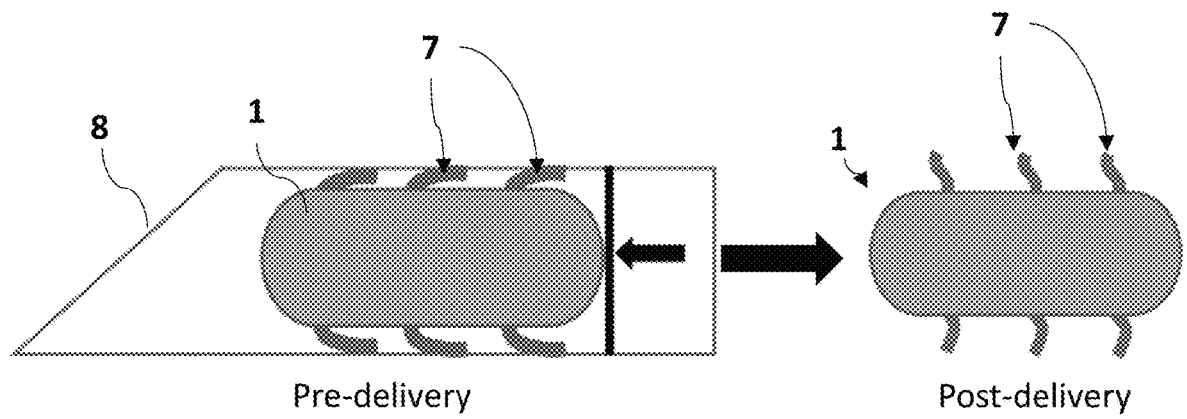
FIG. 3 is a plan view of injection of a tissue implantation device having immobilizers into tissue, and the subsequent expansion of the immobilizers.

In another embodiment, the tissue implantation device comprises two or more immobilizers positioned on an outer surface of the outer shell. After capsule insertion into soft tissue, the immobilizers can engage with the soft tissue to fix the capsule in the soft tissue, and can prevent migration of the capsule in the soft tissue in some cases. FIG. 3 illustrates one embodiment of an immobilizer, where the immobilizer is a resilient arm. As shown on the left of the figure, when tissue implantation device 1 is in a pre-delivery position within a syringe needle bore 8, immobilizer arms 7 are in a retracted position. After the tissue immobilizer is injected into a tissue, the resilient arms extend outward and, in some cases, anchor device 1 into the surrounding tissue, preventing or minimizing movement of device 1.

In some embodiments, the immobilizers comprise one or more holes, depressions, or channels extending inward from the outer surface of the capsule. Such cavities permit tissue growth to occur within these spaces, immobilizing the capsule in the biopsied position.

IL Methods of Imaging a Tissue Implantation Device

In another aspect, a method of imaging a tissue implantation device in a biological environment comprises disposing a tissue implantation device described in Section I herein in a biological environment, the population of ultrasound-switchable fluorophores having a switching threshold in the biological environment; exposing the biological environment to an ultrasound beam to form an activation region within the biological environment; switching the fluorophores in the activation region from an off state to an on state; exciting the ultrasound-switchable fluorophores in the activation region with a beam of electromagnetic radiation; and detecting light emitted by the ultrasound-switchable fluorophores.

Turning now to specific steps of methods, methods described herein comprise disposing a tissue implantation device into an environment. Any environment not inconsistent with the objectives of this disclosure may be used. In some embodiments, the environment is a biological environment. An environment of a method described herein may also be a non-biological environment. In some cases, for example, a biological environment is an in vivo environment, such as a tissue, organ, blood vessel, or other portion of a living organism. In some embodiments, the biological environment comprises a tumor or tumor vasculature. When the tissue implantation device is used as a biopsy clip or localization seed, biological environment can be a tumor boundary and normal tissue. The tumor and normal tissue can be located in any tissue or organ in a living organism, such as breast, lymph, prostate, head, neck, throat, mouth, thyroid, skin, colon, cervix, or uterus. In other cases, a biological environment comprises an in vitro environment, such as a tissue culture. The biological environment of a method described herein can also comprise or be replaced by a biological phantom material or tissue-mimicking phantom material, such as an agar, silicone, polyvinyl alcohol (PVA) gel, polyacrylamide (PAA) gel, or a dispersion of an oil in gelatin. Other phantom materials may also be used.

In some instances, the tissue implantation device is disposed at a depth of 0.1-10 centimeters (cm) below a surface of the biological environment. Moreover, in some embodiments, a biological environment comprises deep tissue. "Deep" tissue, for reference purposes herein, comprises tissue (or, in the case of a phantom material, an interior region of the phantom material) that is located at least about 1 cm below the exterior or outer surface of the organism, tissue culture, or other larger structure associated with the biological environment (such as, in the case of a phantom material, the outer surface of the phantom material). In some embodiments, for instance, deep tissue is located between about 1 cm and about 10 cm, between about 1 cm and about 6 cm, or between about 1 cm and about 5 cm below an outer surface. In some cases, deep tissue is located more than 10 cm below an outer surface. Further, an outer surface, in some embodiments, comprises the surface of the skin of an organism.

The tissue implantation device can be delivered into the biological environment via a needle, where the tissue implantation device is injected into the tissue from the needle at a desired location. In some cases, the needle location can be guided by ultrasound, x-ray, or any other imaging technique.

Methods described herein also comprise exposing an environment, such as a biological environment, to one or more ultrasound beams to create an activation region within the environment. In some instances, one, two, three, or n ultrasound beams are used. The ultrasound beam can have any ultrasound frequency not inconsistent with the objectives of the current disclosure. In some embodiments, an ultrasound beam comprises an oscillating sound pressure wave with a frequency of greater than about 20 kHz or greater than about 2 MHz. In some cases, an ultrasound beam described herein has a frequency of up to about 5 GHz or up to about 3 GHz. In some embodiments, an ultrasound beam has a frequency between about 20 kHz and about 5 GHz, between about 50 kHz and about 1 GHz, between about 500 kHz and about 4 GHz, between about 1 MHz and about 5 GHz, between about 2 MHz and about 20 MHz, between about 2 MHz and about 10 MHz, between about 5 MHz and about 200 MHz, between about 5 MHz and about 15 MHz, between about 200 MHz and about 1 GHz, between about 500 MHz and about 5 GHz, or between about 1 GHz and about 5 GHz.

In addition, an ultrasound beam can have any power not inconsistent with the objectives of the current disclosure. In some embodiments, for instance, an ultrasound beam has a power between about 0.1 W/cm$^2$ and about 10 W/cm$^2$, between about 0.1 W/cm$^2$ and about 5 W/cm$^2$, between about 0.5 W/cm$^2$ and about 5 W/cm$^2$, between about 1 W/cm$^2$ and about 10 W/cm$^2$, or between about 1 W/cm$^2$ and about 5 W/cm$^2$. In other cases, an ultrasound beam has a power between about 100 W/cm$^2$ and about 5000 W/cm$^2$, or between about 100 W/cm$^2$ and about 3000 W/cm$^2$. In some cases, the use of an ultrasound beam having a high power, such as a power described herein, can result in the generation of non-linear effects within the activation region. Moreover, in some embodiments, the effective size of the activation region can be reduced in this manner, leading to improved imaging resolution.

An environment can be exposed to an ultrasound beam in any manner not inconsistent with the objectives of the current disclosure. For example, in some embodiments, a biological environment is exposed to an ultrasound beam described herein for only a limited duration. In some cases, for instance, the ultrasound beam is provided to the environment for less than about 1 second or less than about 500 ms. In some embodiments, the ultrasound beam is provided to the environment for less than about 300 ms, less than about 100 ms, less than about 50 ms, or less than about 10 ms. In some cases, the ultrasound beam is provided to the environment for about 1 ms to about 1 second, about 1 ms to about 500 ms, about 1 ms to about 300 ms, about 1 ms to about 100 ms, about 1 ms to about 50 ms, about 1 ms to about 10 ms, about 10 ms to about 300 ms, about 10 ms to about 100 ms, about 10 ms to about 50 ms, or about 50 ms to about 100 ms. The use of short exposure times of a biological environment to an ultrasound beam, in some embodiments, can permit the time-gating of fluorescence signals, such that a desired USF signal can be temporally separated from one or more undesired or non-analyte fluorescence signals, such as a tissue autofluorescence signal or a signal from a randomly switched-on fluorophore.

Moreover, the ultrasound beam can be a continuous wave beam or a pulsed or modulated beam. The use of a modulated or pulsed ultrasound beam, in some embodiments, can further improve the signal to noise ratio (SNR) of a method described herein by permitting frequency-gated detection of the USF signal. For example, in some cases, a pulsed or modulated ultrasound beam provides an ultrasound exposure having a specific frequency or modulation. As a result, the corresponding USF signal can also exhibit the same specific frequency or modulation. Thus, in some such cases, a lock-in amplifier is used to increase the sensitivity of the detector to the specific frequency or modulation, thus increasing the overall sensitivity and SNR of the method. The use of a modulated ultrasound beam can also improve the temperature resolution of a method described herein, as described further hereinbelow.

In some embodiments of methods described herein, a single ultrasound beam is directed toward the environment using a single ultrasound transducer, such as a high intensity focused ultrasound (HIFU) transducer. In other instances, a plurality of ultrasound beams is directed toward the environment using a plurality of ultrasound transducers. Moreover, in some cases, a first ultrasound beam is directed toward the environment at a first angle and/or from a first direction, and a second ultrasound beam is directed toward the environment at a second angle and/or from a second direction differing from the first angle and/or direction. In some embodiments, for instance, the first and second directions are orthogonal or substantially orthogonal directions, such as directions separated by 80 to 100 degrees. In other cases, the directions are separated by less than 80 degrees or more than 100 degrees. Further, if desired, additional ultrasound beams may also be directed toward the environment from additional directions or at additional angles. In such cases, the focal zones of the beams can overlap or intersect with one another to form an activation region at the intersection of the beams. In this manner, an activation region can have a smaller volume or cross section than the focal zone or cross section of a single ultrasound beam used to generate the activation region, thereby improving imaging resolution. In some cases, for instance, the activation region has a lateral dimension and/or an axial dimension of less than about 10 mm, less than about 9 mm, less than about 8 mm, less than about 7 mm, less than about 6 mm, less than about 5 mm, less than about 4 mm, less than about 3 mm, less than about 2 mm, less than 1.5 mm, or less than about 1 mm. In some embodiments, the activation region has a lateral dimension and/or an axial dimension of less than about 700 µm or less than about 50 µm. In some embodiments, the activation region has a lateral dimension and/or an axial dimension of about 300 µm to about 10 mm, about 400 µm to about 1.5 mm, about 400 µm to about 1 mm, about 400 µm to about 700 µm, or about 400 µm to about 500 µm. In some cases, the lateral and axial dimensions both have a size recited herein, including a size below about 1 mm or below about 700 µm. Moreover, in some embodiments, the lateral and axial dimensions of the activation region are different, thereby providing a relatively anisotropic activation region. Alternatively, in other instances, the lateral and axial dimensions are substantially the same, thereby providing a relatively "square" or isotropic activation region.

An "activation region," for reference purposes herein, comprises a region of the environment in which ultrasound-switchable fluorophores described herein are or can be switched from an off state to an on state. For example, in some cases, an activation region comprises a region of high temperature compared to other portions of the environment. Moreover, as described further herein, the size, shape, and/or other properties of the activation region can be determined by the number and/or power of the one or more ultrasound beams used to form the activation region. In some cases, for instance, the size and shape of an activation region is defined by the focal zone of a single ultrasound beam. In other cases, an activation region is defined by the overlap of the focal zones of a plurality of ultrasound beams.

A fluorophore described herein can be disposed within an activation region in any manner not inconsistent with the objectives of this disclosure. For example, as previously discussed, the fluorophore is disposed in a tissue implantation device described herein. The tissue implantation device can be disposed within an activation region directly by injection. For example, in some embodiments, an ultrasound beam described herein is raster scanned across or within an environment, thereby producing a plurality of activation regions in different locations within the environment in a sequential manner.

Methods described herein also comprise exposing an environment to a beam of electromagnetic radiation and/or exciting at least one fluorophore in an on state with a beam of electromagnetic radiation. A fluorophore can be excited with a beam of electromagnetic radiation in any manner not inconsistent with the objectives of the current disclosure. In some embodiments, for instance, a fluorophore is excited using a laser excitation source such as a diode laser. In other instances, a fluorophore is excited using one or more light emitting diodes (LEDs) or a broadband excitation source. Moreover, an excitation source described herein can provide any wavelength of light not inconsistent with the objectives of the current disclosure. In some embodiments, a fluorophore described herein is excited with a beam of electromagnetic radiation comprising visible light (such as red light), NIR light, or IR light. In other cases, the beam of electromagnetic radiation comprises ultraviolet (UV) light. In some embodiments, a fluorophore described herein is excited with a beam of electromagnetic radiation comprising a wavelength maximum of approximately 671 nm, 730 nm, 800 nm, or 810 nm. The fluorophore can also be excited with a beam of electromagnetic radiation having a wavelength between 600 nm to 900 nm, 650 nm to 850 nm, 700 nm to 800 nm, 600 nm to 800 nm, 600 nm to 700 nm, 700 nm to 900 nm, 800 nm to 900 nm, 900 nm to 1000 nm, 1000 nm to 1100 nm, 1100 nm to 1200 nm, 1200 nm to 1300 nm, 1400 nm to 1500 nm, or 1600 nm to 1700 nm.

Methods described herein also comprise detecting a photoluminescence signal or other light emitted within an environment or within a specific location within an environment. In some embodiments, for instance, a method comprises detecting light emitted by at least one ultrasound-switchable fluorophore present in the tissue implantation device. Light emitted by the fluorophore can be detected in any manner not inconsistent with the objectives of the current disclosure. In some embodiments, for example, detecting light emitted by at least one fluorophore in an on state comprises detecting the light in a time-gated or frequency-gated manner, including a time-gated manner or frequency-gated manner described herein. In some cases, the light emitted by the at least one fluorophore in the on state is detected after a time delay that is longer than the fluorescence lifetime of the fluorophore in the off state or longer than the fluorescence lifetime of another species present in the biological environment. For example, in some embodiments, the light emitted by the at least one fluorophore in the on state is detected after a time delay that is longer than the autofluorescence lifetime of a non-fluorophore species present in the biological environment, such as the autofluorescence lifetime of tissue, which may be up to about 4 ns or up to about 5 ns.

In addition, the photoluminescence signals of a method described herein can be detected using any detector configuration not inconsistent with the objectives of the current disclosure. In some embodiments, for instance, a photoluminescence signal is detected using a detector comprising a plurality of optical fiber collectors coupled to a camera or photon counter, such as a charge coupled device (CCD) or a photomultiplier tube (PMT). Further, in some cases, the optical fiber collectors are spatially distributed around the environment or around a detection surface of the environment (such as skin or another exterior surface of the environment). Any desired number of optical fiber collectors can be used. In some embodiments, up to 30, up to 20, or up to 10 optical fiber collectors are used. In some cases, 4-30, 4-20, 6-30, 6-20, 8-30, 8-20, 10-30, or 10-20 optical fiber collectors are used. Other configurations are also possible.

Additionally, in some cases, a plurality of photoluminescence signals at a plurality of locations within an environment is detected by raster scanning the environment. Such raster scanning can include raster scanning of one or more ultrasound beams across or within the environment, such that the ultrasound beam sequentially generates a series of activation regions at different locations within the environment. It is also possible, in some instances, to use a portable detector, which can be moved or scanned from location to location within the environment. Moving or scanning a portable detector in such a manner can increase the detection area of the method. In other cases, a two-dimensional detector such as a charge-coupled device (CCD) image sensor or camera is used to detect photoluminescence signals at a plurality of locations simultaneously.

Methods described herein can further comprise correlating a size, shape, position, orientation, or any combination thereof, of the tissue implantation device in the biological environment based on the detected light emitted by the ultrasound-switchable fluorophores. For example, as described in more detail below in the Examples, the size, shape, position, and/or orientation of the tissue implantation device can be correlated by the location, intensity, and frequency of the emitted light captured by an imager.

In some embodiments, methods described herein can comprise disposing two or more tissue implantation devices in the biological environmental, and resolving the two or more tissue implantation devices by detecting the light emitted by the ultrasound-switchable fluorophores. In some cases, the two or more tissue implantation devices can have the same or different switching thresholds, but all have the same or different USF fluorophores having the same peak emission wavelength. In such cases, a tumor boundary can be delineated. However, in other embodiments, the two or more tissue implantation devices each comprise a different USF fluorophores having the same or different switching thresholds, but each having a different peak emission wavelength. In such embodiments, multiplex USF imaging can be performed. When the peak emission wavelengths are different, multiple devices can not only delineate tumor boundaries, but can also be used to encode tumor orientation.

Some embodiments described herein are further illustrated in the following non-limiting Examples.

Example 1

Ultrasound Switchable Fluorophores

Targeting ultrasound-switchable fluorophores suitable for use in some embodiments of methods described herein are prepared and used as follows. In one embodiment, ultrasound-switchable fluorophores suitable for use in some embodiments of methods described herein are prepared in a manner described in U.S. Patent Application Publication No. 2015/0309014 to Yuan et al. ("the '014 publication"), which again, is incorporated herein in its entirety.

Figure 4:
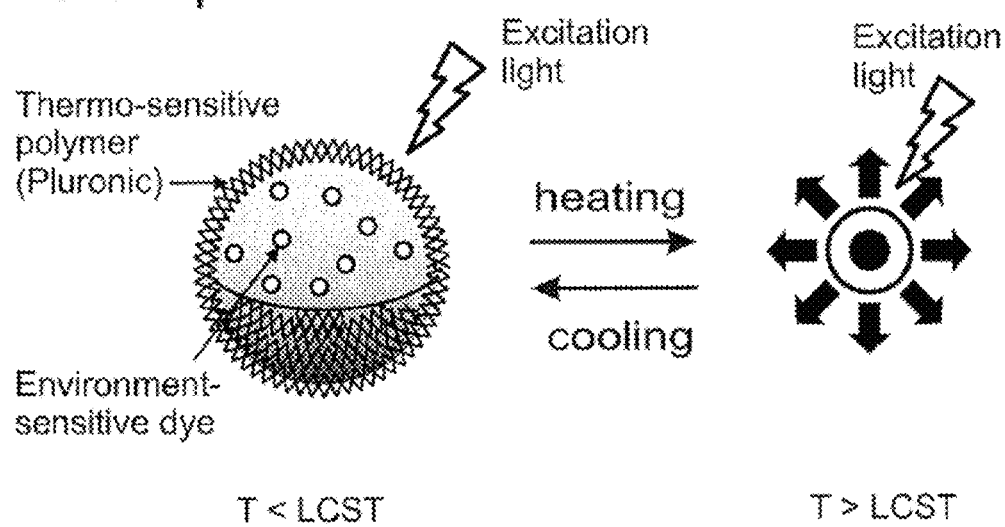
FIG. 4 illustrates a thermal switching event of an ultrasound-switchable fluorophore.

As described above, this disclosure relies generally on ultrasound fluorescence (USF or USFM) imaging. As understood by one of ordinary skill in the art and as described above, USF commonly operates according to the following principles. When an environment-sensitive near infrared (NIR) fluorescent dye (such as ZnPC, ADP(CA)$_2$, ICG, among others) is encapsulated into a thermo-sensitive nanoparticle (made by made by Pluronic F127, F98, F98-PEG20k, F98-PEG30k, F98-PEG40k, F68 and its PEGylated polymers, among others), the dye's fluorescence emission exhibits a switch-like function of the temperature (FIG. 4). Briefly, when the temperature is below a threshold ($T<T_{th1}$), the nanoparticle exhibits hydrophilicity and provides a water-rich, polar, and non-viscous microenvironment in which the dye shows very low emission efficiency (so-called OFF). When T is above another threshold ($T>T_{th2}$), the nanoparticle exhibits hydrophobicity and provides a polymer-rich, non-polar, and viscous microenvironment in which the dye shows strong emission (so-called ON). When the transition bandwidth ($T_{BW}=T_{th2}-T_{th1}$) is narrow, the fluorescence intensity appears a switch function as the temperature. The first threshold ($T_{th1}$) is also known as LCST (the lower critical solution temperature of the thermo-sensitive nanoparticles). In USF imaging, the threshold $T_{th1}$ can be controlled slightly above the tissue background temperature ($T_{BG}$) (i.e. $T_{BG}<T_{th1}$) to maintain an OFF state (FIG. 5(a)). For example, $T_{th1}=38°$ C. is above $T_{BG}=37°$ C. (body temperature). When the focused ultrasound is applied, the tissue temperature (T) at the focus will be increased above the threshold ($T>T_{th1}$) to switch on the fluorophores (FIG. 5(b)). The USF agents outside the focus remain off. A high-resolution USF image can be formed via point-by-point scanning of ultrasound focus.

Figures 5A, 5B:
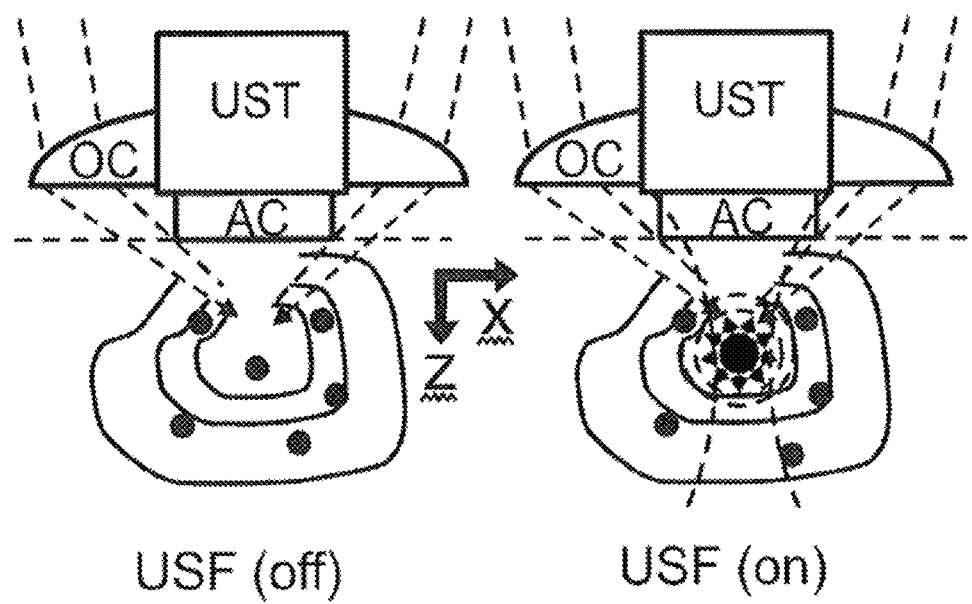
FIGS. 5A and 5B schematically illustrate steps of a method of forming an activation region.

In USF imaging, NIR excitation light is delivered into centimeters deep tissue via light scattering (see the curves in FIGS. 5(a) and 5(b)). When ultrasound is off, no or weak fluorescence is emitted although the excitation light is on (see FIG. 5(a)). When ultrasound is on, the USF contrast agents in the ultrasound focal volume can be switched on to emit fluorescence (see the dashed circles in FIG. 5(b)). The emitted NIR photons can propagate out of the tissues via light scattering (towards all directions). All the ultrasound-induced fluorescence photons are signal and should be collected as many as possible. FIGS. 5(a) and 5(b) show the cross section of the sample (i.e. on x-z plane).

In USF imaging, only ultrasound-induced fluorescence photons are used as the signal. These photons can be generated only from the region around the ultrasound focus. Thus, the spatial resolution of USF depends on the size of this region. The thermal energy can be confined into the ultrasound focal region when the ultrasound exposure time is shorter enough than the thermal diffusion time (i.e. so-called thermal confinement). Unlike pure ultrasound or photoacoustic imaging (f-number usually >2), USF uses an ultrasound transducer with a small f-number (<1) to reduce the focal size. In addition, USF contrast agents can be switched on only in a region where ultrasound energy is above the switching-on threshold ($T_{th1}$). The existence of this threshold makes the region is usually smaller than the actual size of the ultrasound-induced thermal focus. Lastly, if nonlinear acoustic effect occurs, both lateral and axial focal sizes can further shrink.

NIR-I region can cover 670-900 nm. Therefore, appropriately selecting NIR-I fluorophores (for USF contrast agents) with different excitation (Ex) and emission (Em) wavelengths permits multi-color (multiplex) imaging to be conducted in the NIR-I region. For example, Color-1 can be selected as Ex=671 nm and Em=680-710 nm; Color-2 can be Ex=730 nm and Em=740-770 nm; and Color-3 can be Ex=810 nm and Em>840 nm (See FIGS. 6A and 6B). Although spectral cross talk may be possible, several strategies can be adopted to minimize or unmix them, as described further hereinbelow. Thus, USF can simultaneously identify multiple targets via multi-colors, which will significantly increase the specificity to the targets (none of CT, MRI, PET and ultrasound has this capability).

The NIR-II region can cover 900-1700 nm. In some embodiments, a NIR-II fluorophores (for USF contrast agents) can be selected having different excitation (Ex) and emission (Em) wavelengths that permit multi-color (multiplex) imaging to be conducted in the NIR-II region. For instance, Color 4 can be selected as Ex=800 nm and Em=912 nm. In some embodiments, a combination of both NIR-I and NIR-II fluorophores can be used.

Figure 6A:
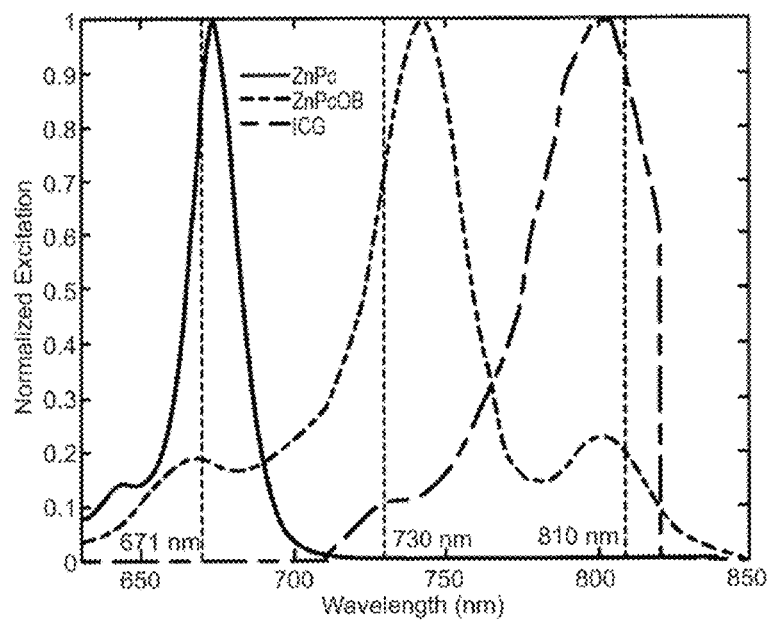
FIG. 6A is a plot of excitation profiles for a series of ultrasound-switchable fluorophores.

There are two common types of spectral cross talk. The first one is so-called "one laser excites multiple fluorophores" cross talk, due to the excitation spectrum overlap. For example, when the 671-nm laser is on, it may excite both ZnPc and ZnPcOB (FIG. 6A). This type of cross talk can be reduced or avoided via sequentially turning on each laser-camera pair, as described further hereinabove and hereinbelow. Briefly, the USF system can sequentially turn on each laser-camera pair via an accurate electronic triggering system. For example, the Color-1 channel's camera is triggered ON and will detect the emission mainly from ZnPc. In contrast, the Color-2 and Color-3 channel's cameras are OFF, so the emission from ZnPcOB (excited by the 671-nm laser) will not be detected. Similarly, this rule is true for the other two laser-and-camera pairs.

The second type of cross talk is so-called "spectral bleed-through" cross talk, caused by the emission spectrum overlap. This cross talk can lead to emission leakage from one fluorophore channel to another (see the arrows in FIG. 6B). For example, when the 671-nm laser is on and possibly excites both ZnPc (strongly) and ZnPcOB (weakly), a small part of the emission from ZnPcOB (belongs to Color-2) may leak into Color-1 channel's camera (it is the only camera that is turned on at this moment) because of the emission spectral overlap. This type of cross talk can be minimized via carefully selected emission filters and excitation light wavelengths. This type of cross talk may also be minimized or eliminated via a signal processing method, as described further herein. Also, if needed, any unavoided spectral leakage can be quantified prior to temperature measurement by using tissue phantoms and/or in vivo tissues, and then taken into account in further signal processing.

Additionally, gas-filled micro-particles, such as microbubbles, can generate a short but high temperature pulse in and around the particle surface when the microbubble is irradiated with an ultrasound pulse at diagnostic intensity level. This short temperature pulse spatially decays very fast (only ~0.2° C. left at a distance of 1 micron away from the bubble surface). In USF imaging, tissue overheating caused by microbubbles is minimalized from this fast temperature decay. However, this microscopic heating principle is very useful for heating ultrasound switchable fluorophores, because ultrasound switchable fluorophores are small nanoparticles that can be attached on the microbubble's surface. For example, ultrasound switchable fluorophores (e.g. USF contrast agents) can be attached to a surface of a microbubble or thermo-sensitive polymer through a biotin/streptavidin, or other common linkages.

A highly ultrasound-absorbing polymer, biodegradable polyurethane with pendent carboxyl groups (PU—COOH), silicone, or other ultrasound energy absorbing material can alternatively be used instead of the microbubbles. Using ultrasound-absorbing polyurethanes as an example, such polyurethanes make relatively rigid gas-filled sub-microparticles that are smaller in diameter (~700 nm in diameter) that are smaller than the microbubbles. These relatively rigid particles are also much more stable than microbubbles, and their acoustic attenuation is significantly reduced because of smaller size. More importantly, these particles can be efficiently heated for USF imaging because of ~22 times higher in acoustic absorption, ~2.3 times lower in specific heat capacity, ~3 time lower in thermal conductivity compared with soft tissue. Similar to the microbubbles, biotin can be incorporated onto the surface of the ultrasound-absorbing polyurethanes, and the USF contrast agents can be attached using the streptavidin linkage.

Example 2

Fabrication of a Tissue Implantation Device

Figure 7:
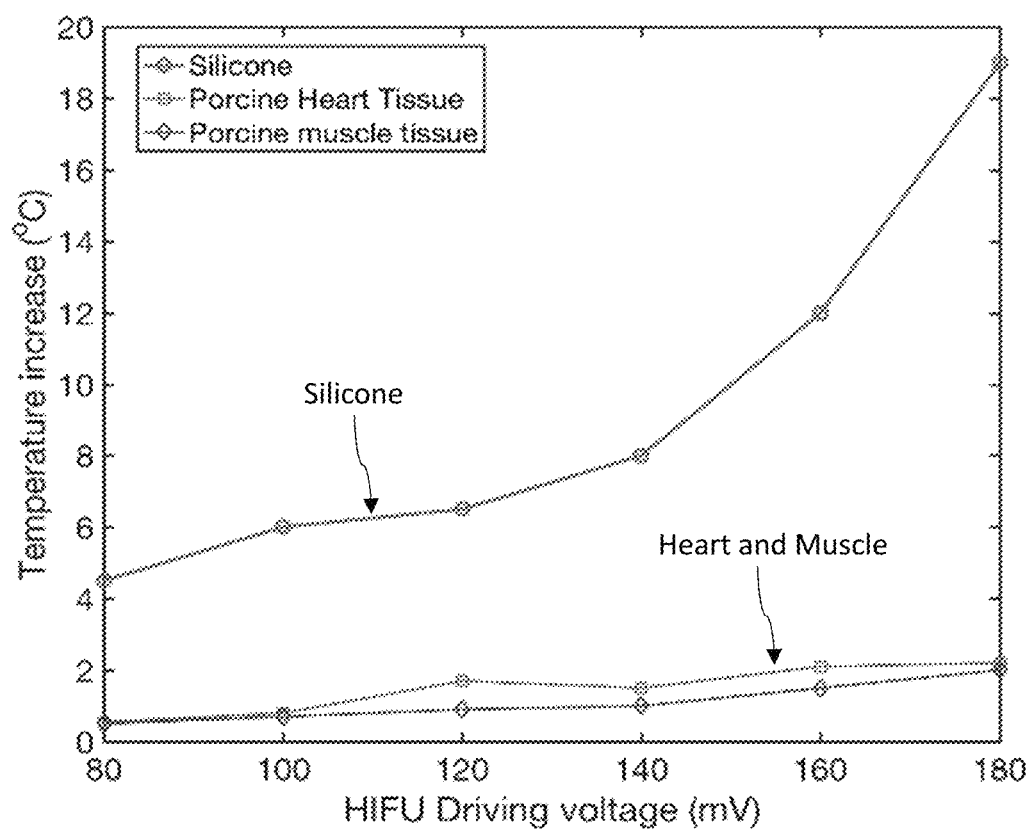
FIG. 7 is a plot of a temperature increase of silicone verses porcine heart and muscle tissue when exposed to ultrasound energy.

Silicone has ~8-10 times higher acoustic-to-thermal conversion efficiency compared with soft tissues. Ultrasound-induced temperature increase ($\Delta T$) in silicone, porcine muscle tissue, and porcine heart tissue was measured to evaluate the efficacy of using silicone as an in ultrasound energy absorbing material in the construction of a tissue implantation device. All the experimental parameters were maintained the same between each material. As shown in FIG. 7, $\Delta T$ is determined principally by material properties. Compared with porcine muscle and heart tissues, the $\Delta T$ in silicone is ~8-10 times higher. This agrees with theoretical estimation (~8 times higher) based on parameters reported in literature. Thus, assuming temperature increase in silicone is 2° C., the same ultrasound pulse will only increase tissue temperatures by ~0.2-0.25° C., which is within safe levels—i.e. no damage to the tissue is expected.

While silicone was chosen as the exemplary ultrasound energy absorbing material to show proof of concept in this example, it is believed that other ultrasound energy absorbing materials would also display similar properties, such as polyurethanes, polydimethylsiloxanes (PDMS), various polymer-gels, combinations of different materials, or any other ultrasound energy absorbing material.

Heating the wall of a small silicone seed is much efficient and faster than heating a piece of tissue. USF methods can be conducted with a mechanical index (MI) and thermal index (TI) well below the FDA-required safety limits of MI<1.9 and TI<6. Moreover, compared with conventional USF imaging, imaging speeds for the tissue implantation device can be much faster. The small silicone capsule can be rapidly heated without significant changes in the temperature of surrounding tissue. USF agents are highly confined in the tissue implantation device, so the surrounding tissue does not generate USF signal.

Figure 8A:
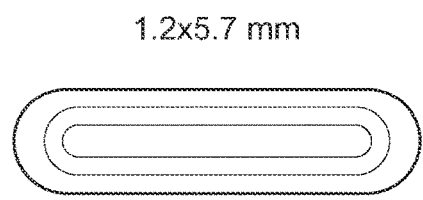
FIG. 8A is a plan view of a silicone-based tissue implantation device.

A tissue implantation device was prepared using silicone as the ultrasound energy absorbing material to form a capsule having dimensions of 1.2×5.7 mm and a central receiving space having an internal diameter (ID) of approximately 0.64 mm. The capsule is shown in FIG. 8A. ICG-based USF contrast agent was placed in the central receiving space through injection, giving a final capsule configuration illustrated in FIG. 1A.

Example 3

X-Ray Contrast of Tissue Embedded Tissue Implantation Device

Figure 8B:
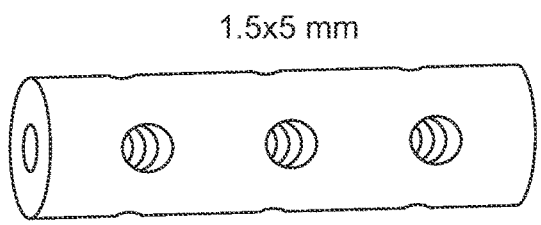
FIG. 8B is a plan view of a Beacon® biopsy clip made of polyetherketoneketone (PEKK) polymers.
Figure 8C:
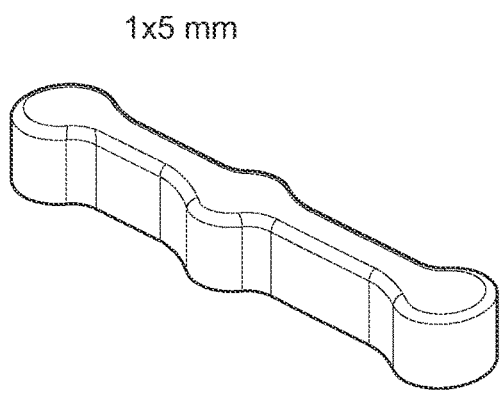
FIG. 8C is a perspective view of a BiomarC® clip made of pyrolytic carbon coated (PCC) ceramic.
Figure 8D:
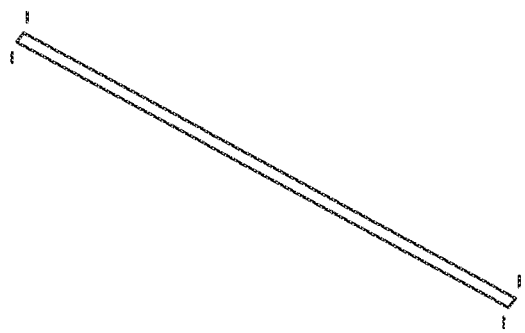
FIG. 8D is a perspective view of a stainless steel needle.
Figure 9:
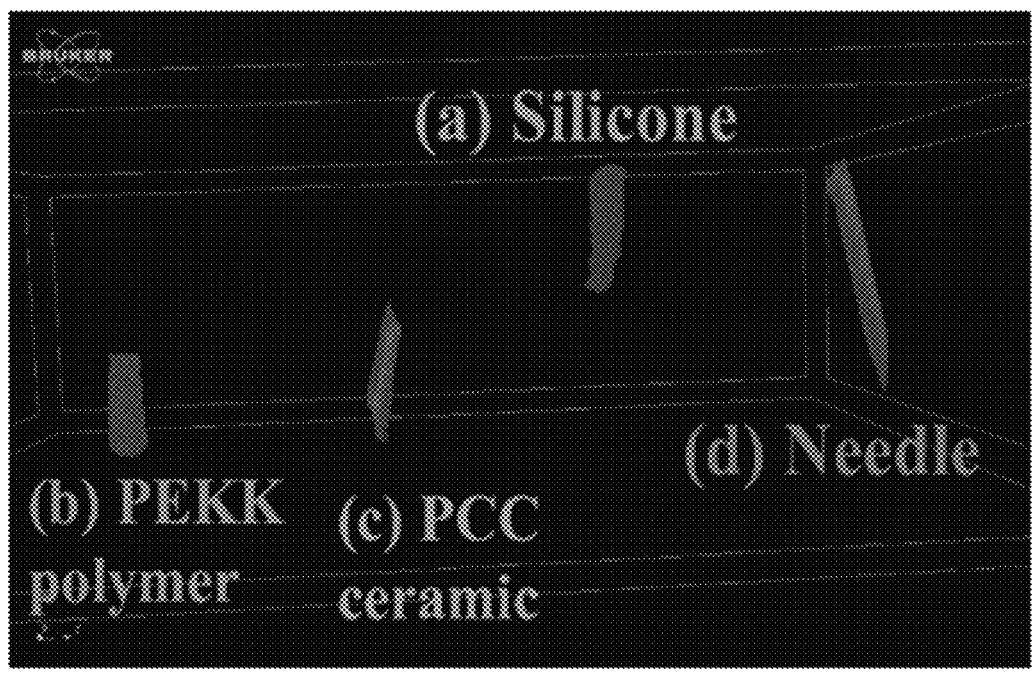
FIG. 9 is computed tomography (CT) image of the four devices of FIGS. 8A-8D embedded in tissue.

X-ray contrast of the silicone-based tissue implantation device prepared in Example 2 was compared with various commercial clips. Specifically, the device was compared with two commercialized clips: PEKK polymer-based Beacon® clip (FIG. 8B, 1.5×5 mm) and PCC ceramic-based BiomarC® clip (FIG. 8C, 1×5 mm), and a stainless steel needle (FIG. 8D). The tissue implantation device was inserted into a piece of pork muscle and imaged with by CT (Skyscan 1178, Bruker) As shown in FIG. 9, all four examples can be clearly resolved using CT.

Example 4

USF and CT Visualization of Tissue Embedded Tissue Implantation Device

Figure 10:
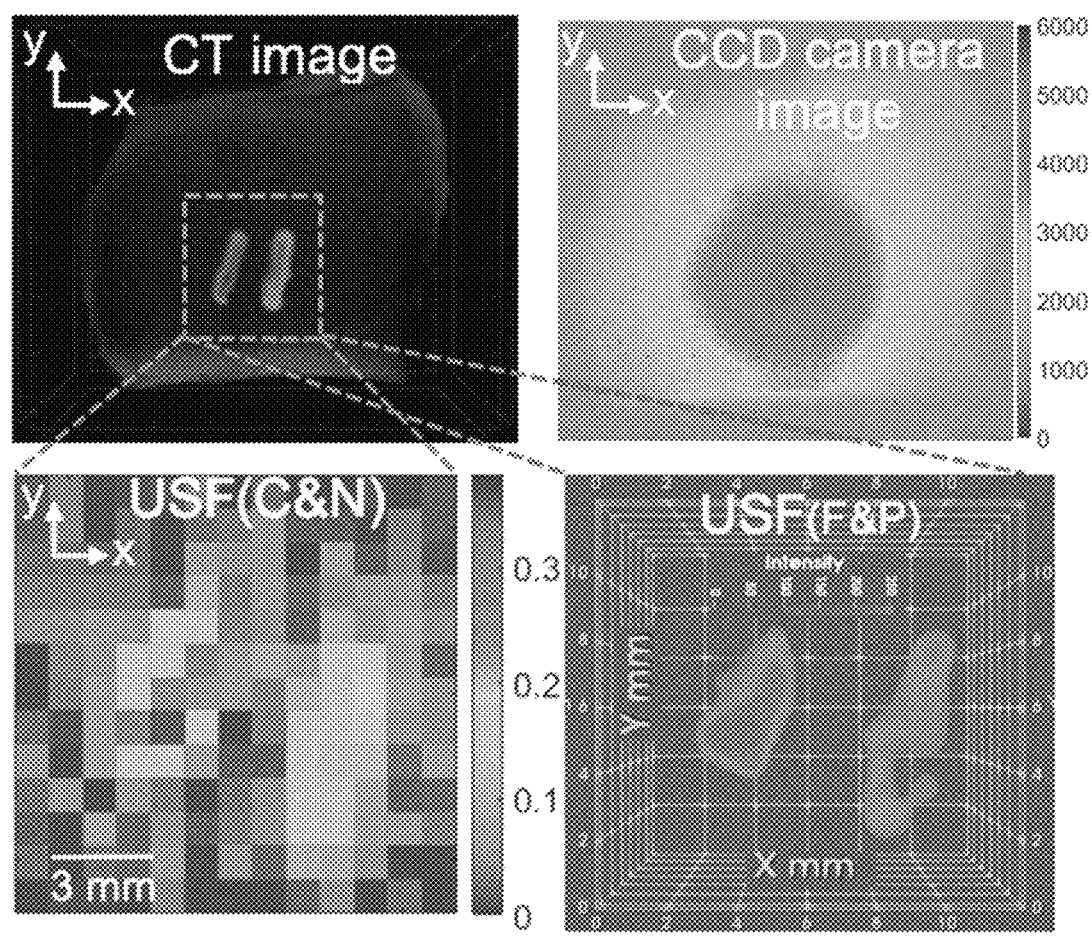
FIG. 10 is images of two silicone-based tissue implantation devices embedded into centimeters deep tissue from CT, a fluorescence camera, USF with raw data, and USF with processed data.

Two silicone-based tissue implantation devices with a separation distance of ~5 mm were embedded approximately 4 cm deep tissue, and images were acquired using CT, a fluorescence camera (denoted as CCD camera image), USF with raw data (denoted as USF (C&N)), and USF with processed data (denoted as USF (F&P)), as respectively shown in FIG. 10. Compared with the CT image, the two USF images correctly show the two tissue implantation devices with appropriate accuracy about the size, shape, position, orientation, as well as the separation distance of between the two tissue implantation devices. In contrast, the fluorescence image acquired by the camera cannot resolve the two tissue implantation devices. However, the fluorescence image can provide a rough horizontal location of the two tissue implantation devices on the X-Y plane, which can narrow the USF scanning region.

Figure 11A:
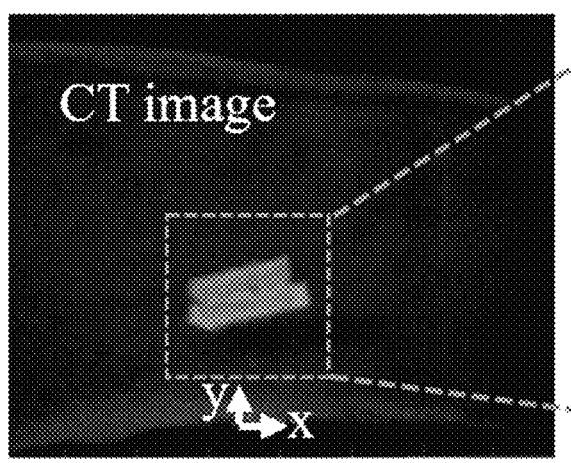
FIGS. 11A and 11B are images of two silicone-based USF tissue implantation devices embedded into deep tissue acquired from CT (FIG. 11A) and USF (FIG. 11B).
Figure 11B:
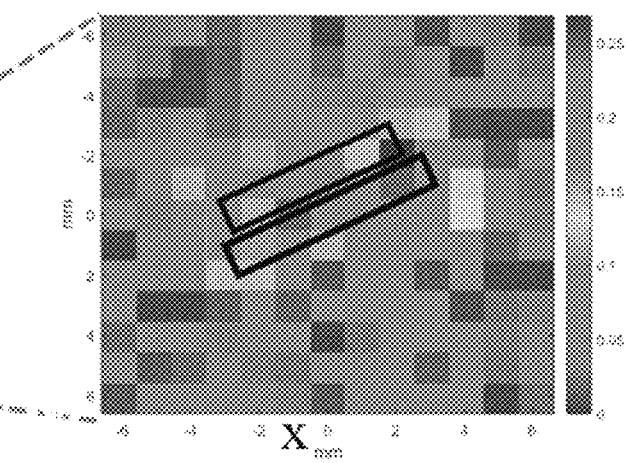

FIGS. 11A and 11B respectively show a micro-CT image and a USF image of two USF silicone-based tissue implantation devices embedded in deep tissue. The two device are positioned next to each other, but can still be roughly resolved on the CT image due to its high spatial resolution (85 μm). Although the two devices are not individually resolved on the USF image, the devices can be clearly seen and accurately localized (i.e. XYZ coordinates can be found), and the shape and size of the devices can be correctly estimated based on the USF image.

Example 5

Handheld USF Imager

Figure 12:
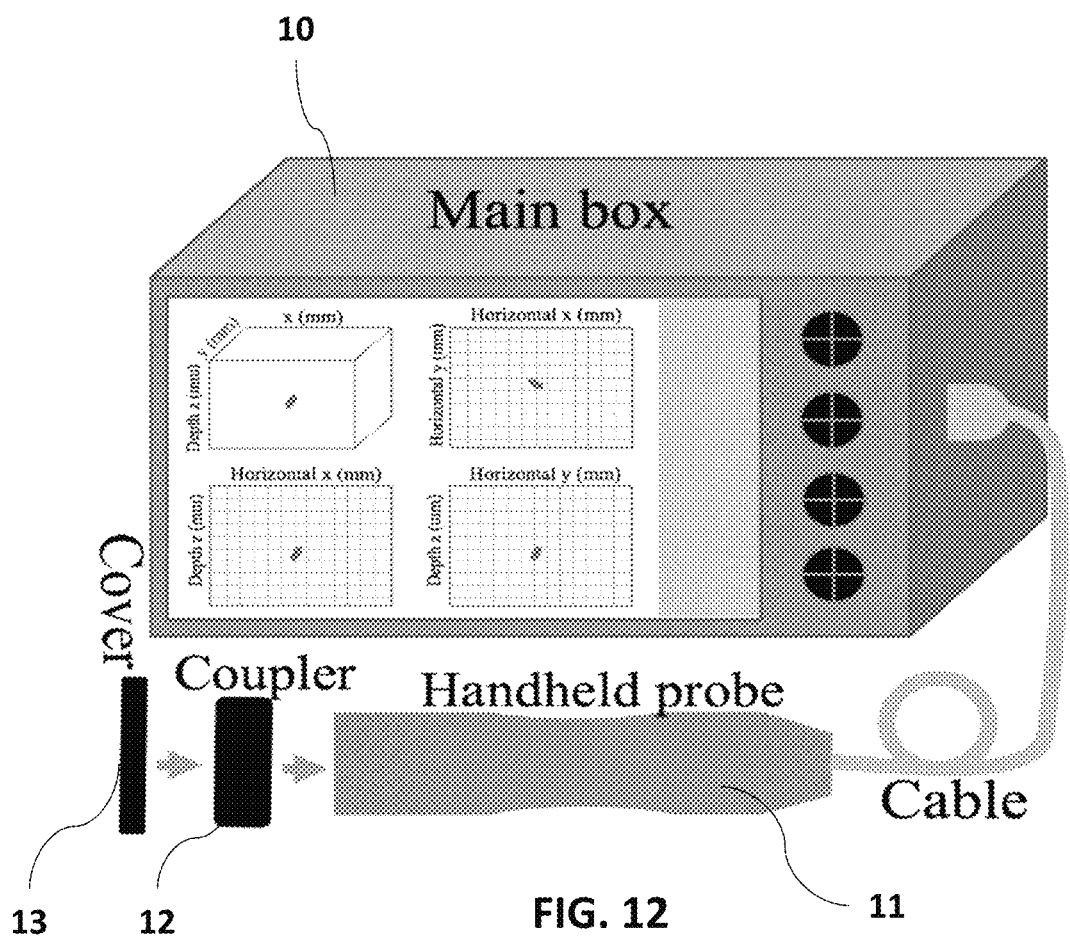
FIG. 12 is a perspective view of a handheld USF imager.

As previously discussed herein, one of the advantages of using the USF-based tissue implantation devices is that the USF imager can be much more compact and portable compared to other imaging methods, such as CT. FIG. 12 shows an embodiment of an exterior design for a handheld USF imager comprising a main box 10; a handheld probe 11; an ultrasound coupler 12; and an optional protective cover 13. The main box 10 comprises and encloses all the optical, ultrasonic, electronic, computing and display components present in a USF imager. The handheld probe 11 encloses an ultrasound transducer array and optical delivery/receiving fibers. The ultrasound coupler 12 provides optimal contact with skin or tissue, and couples ultrasound waves into tissue. The coupler 12 can also have x and y scales on the edges for marking a lesion's x-y position on the skin, which can then be used to determine the best incision position. For safety, when the probe is not used, the optional cover 13 can be put on the tip of the probe or coupler. A screen and a few buttons/switches can be designed on the main box 10 to control the ultrasound, optical and electronic parameters.

Figure 13:
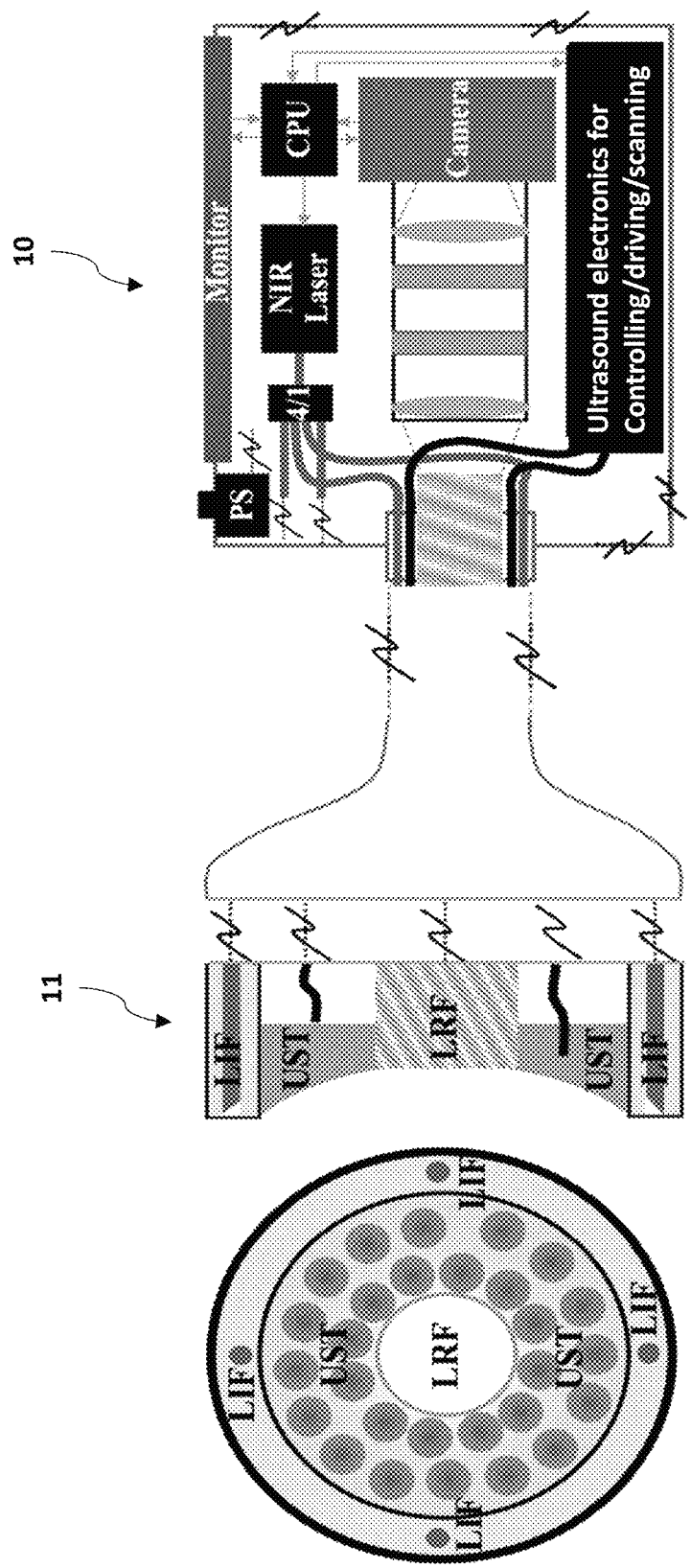
FIG. 13 is a schematic view of the handheld USF imager of FIG. 12.

FIG. 13 shows an exemplary schematic of the handheld USF imager shown in FIG. 12. Four principle sub-systems comprise an ultrasound system; a light illumination system; a light receiving system; and a computing/controlling/displaying system.

For the ultrasound system, an ultrasound transducer (UST) array with a central hole can be used. Unlike conventional ultrasound imaging, a USF imager described herein only needs to deliver ultrasound wave into tissue for exciting USF signals, and is not required to receive ultrasound echoes. Thus, the controlling/driving/scanning system can be much simpler than traditional ultrasound systems. However, ultrasound receiving functionalities can be included in some embodiments, to provide a single imager with multiple functionalities.

The light illumination system can include a NIR light source (such as laser, laser diode) as the excitation light source. The light beam can be split into multiple beams and delivered into tissue via multiple light illumination fibers (LIFs) located at different positions on the handheld probe. The number of light beams and corresponding number of LIFs can vary and is not limiting. In the example shown in FIG. 13, the light beam is split into four beamlets that are delivered into the tissue via four LIFs.

For the light receiving system, emitted fluorescence light from the USF-based tissue implantation device will be collected via at least one light receiving fibers (LRF), which are generally positioned at or near the center of the ultrasound transducer array through the hole. The collected photons can be collimated and filtered and eventually detected by a sensitive imager, such as a CCD or CMOS sensor and/or a photomultiplier tube (PMT).

A central processing unit (CPU) or a computer can be used to acquire the spectrascopic data, compute the image and location, control the electronic system and display the data/image on a monitor. A power supplier (PS) can provide power to the entire system.

Example 6

Methods of Localizing an Embedded Tissue Implantation Device

Generally, the tissue implantation device prepared in Example 2 can provide faster localization than conventional USF imaging. For example, the silicone material comprising the capsule will absorb ultrasound energy much faster than the surrounding tissue due to the inherently higher acoustic-to-thermal conversion efficiency of silicone to soft tissue (See FIG. 7). The USF contrast agent is highly confined in the capsule, so surrounding tissue will not generate USF signal. Thus, a broad, coarse localization scan can be performed to generally (or roughly) locate the capsule. After the general location of the capsule is established, a more targeted, fine localization scan can be performed on a smaller area. The coarse and fine localization modes are discussed in more detail as follows.

When tissue volume is large or prior information concerning the rough location of the tissue implantation device is unclear, a coarse localization (C.L.) "Mode I" can be performed, where ultrasound is either turned off or weakly focused (FIGS. 14A and 14B), depending on the optical signal strength. Thus, the field of view will be large and the region in which the device is possibly located can be quickly found via a blurred optical spot (i.e. no much resolution, see CCD camera image in FIG. 10). This will provide a rough location on x-y plane and can reduce the time needed for searching the device using the high-resolution mode. Mode I can be also used for confirmation of the existence of the device when the high spatial resolution is not required.

Figure 14D:
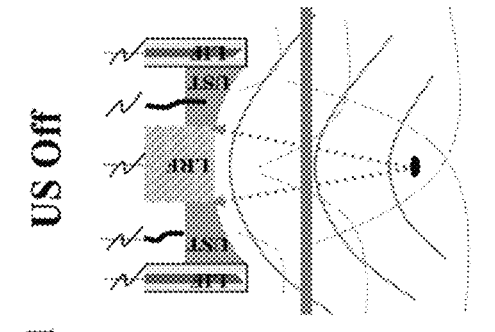
FIGS. 14A-14D are cross-sectional views of coarse and fine localization of embedded tissue implantation devices embedded in tissue.
Figure 14C:
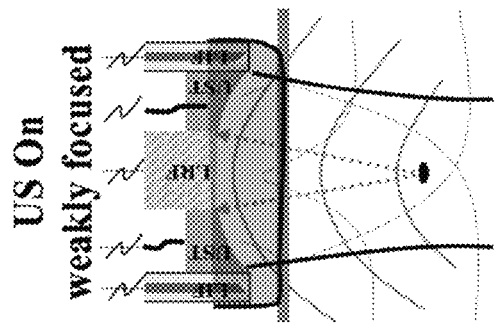
Figure 14B:
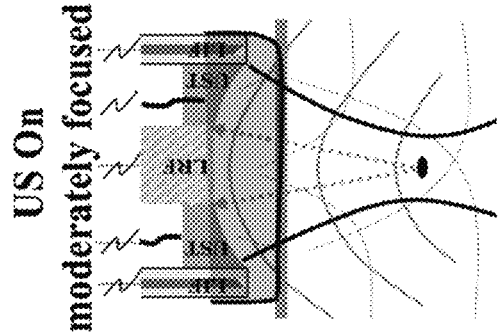
Figure 14A:
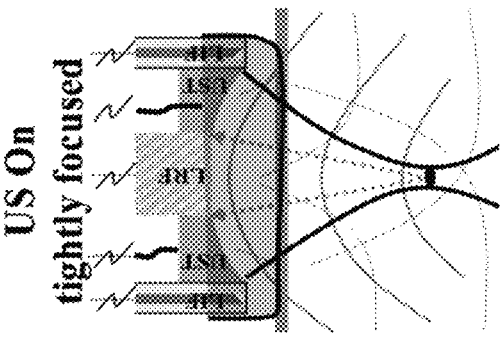

When the rough location of the tissue implantation device is known via either the Mode (I) or other information (such as the medical record about the biopsy region), the system can be switched to Mode (II) for fine localization (F.L.) by confining the scanning within the selected region. In Mode (II), the ultrasound beam is either moderately or tightly focused (FIGS. 14C and 14D). The ultrasound focus can be quickly and 3-dimensionally scanned via the scanning system described in Example 5. Thus, Mode (II) can provide accurate position and depth of the clip/seed and display the information on the screen for guidance. If multiple devices are implanted to delineate lesion boundary, all their locations will be acquired and displayed. Note that the screen on the main box can show the clip/seed positions via at least four formats: 3-D xyz, 2D xy, 2D xz and 2D yz, respectively. The plane of xy is defined as the plane that is parallel to the cross-section of the handheld probe. The depth z is defined as the distance from the probe tip, which is touching with the skin or tissue, to the position of the device. Once the device is located, an incision location can be selected and made. A probe can be inserted into the incision for further localization during the surgery or placed at a side location for continuously monitoring the location of the device.

Example 7

Operational Protocol for Embedding and Visualizing Embedded Tissue Implantation Devices One operational protocol embodiment for embedding a tissue implantation device of Example 2 is delivery of the device into tissue via a needle under guidance of ultrasound or x-ray. After delivery, the device can be confirmed with at least two imaging modalities such as through USF and ultrasound, or through USF and x-ray.

Figures 15A, 15B, 15C, 15D:
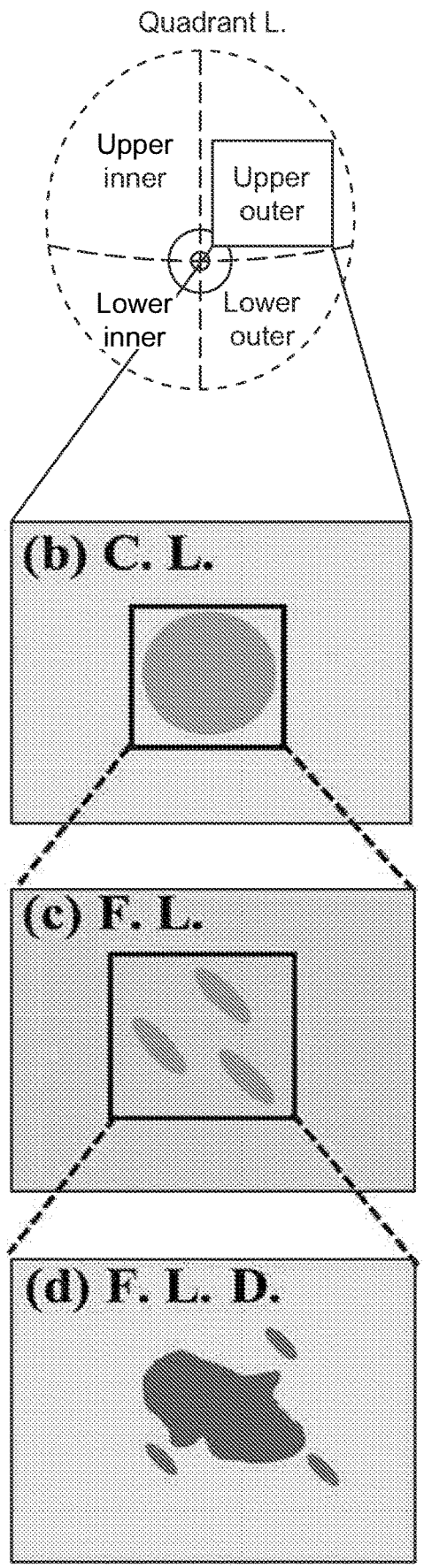
FIGS. 15A-15D illustrate procedures of visualizing embedded tissue implantation devices in tissue.

FIGS. 15A-15D illustrate a general procedure for localization identification and visualization of an implanted tissue implantation device. If a lesion's quadrant location is known (FIG. 15A), such as from medical records, biopsy, diagnostic images, etc., an ultrasound probe, such as probe 11 described in Example 5, can be positioned on this quadrant and setup as Mode (I) (see Example 6) to identified a lesion's rough region via a blurred optical spot (FIG. 15B, C.L.). If the quadrant is unknown, four quadrants can be scanned quickly using Mode (I). Once the quadrant and the region are found, the ultrasound probe will be positioned on the top of the selected region and setup as Mode (II) (see Example 6) to find relatively accurate x, y and z positions (FIG. 15C, F.L.). Since the scanning step size can be controlled, if more accurate results are needed (such as differentiating multiple clips/seeds), a finer scan in the region can be achieved (FIG. 15D, F.L.D., optional). Once the seeds are located, a surgeon can optionally mark the x-y locations of the seeds on the skin. Based on this location information, an optimal or preferred incision location can be identified. After the incision is made, the ultrasound probe can be inserted into the incision for continuously acquiring new locations until the lesion or target tissue is removed. Tissue samples can optionally be scanned with the USF system to confirm the presence of the tissue implantation device, sent to a pathology lab. At the pathology lab, the sample can be rescanned with the USF system to confirm the presence of the device in the tissue, and pathological slides can be prepared based on the confirmed locations.

Example 8

Multiplex Imaging of Tissue Implantation Devices

Figure 6B:
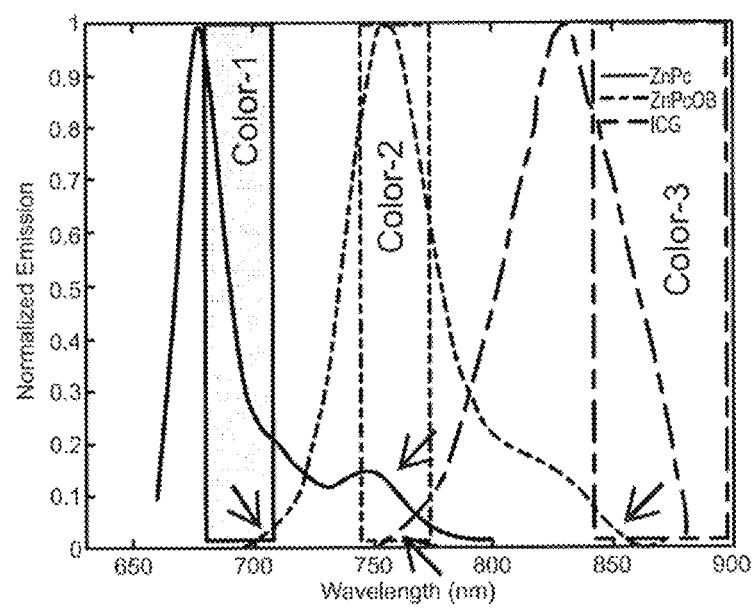
FIG. 6B is a plot of emission profiles for a series of ultrasound-switchable fluorophores.

In instances where multiple tissue implantation devices are used, where each have the same or different USF contrast agents with the same peak emission wavelengths, implantation of these tissue implantation devices can be used to delineate a tumor boundary. However, in some instances, multiple tissue implantation devices can be used where each device has a USF contrast agent having different peak emission wavelengths. For example, as illustrated in FIG. 6B, different USF fluorophores (such as ICG, ZnPc, ZnP-cOB, etc.) have different peak emission wavelengths, which can be differentiated from each other. When different USF contrast agents are used in different tissue implantation devices, not only can tumor boundaries be delineated, but tumor orientation can also be encoded and tracked using multiplex USF imaging.

Figure 16:
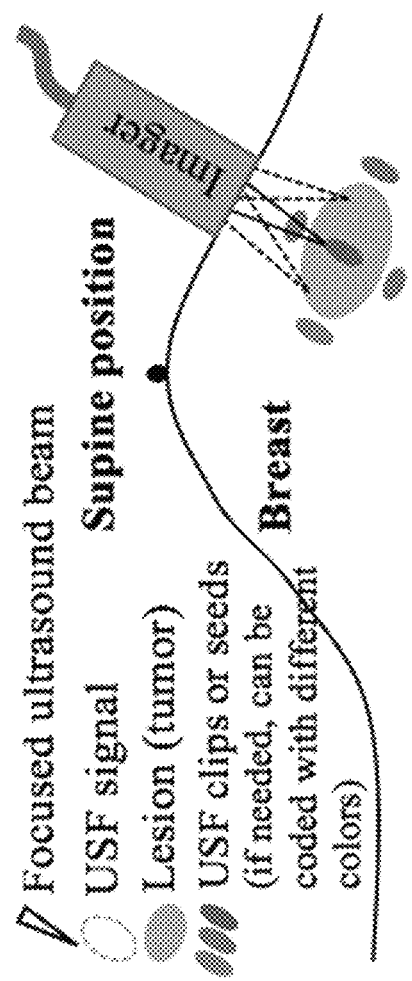
FIG. 16 illustrates a method of imaging of multiple tissue implantation devices having USF contrast agents with the same or different peak emission wavelengths.
Figure 16:
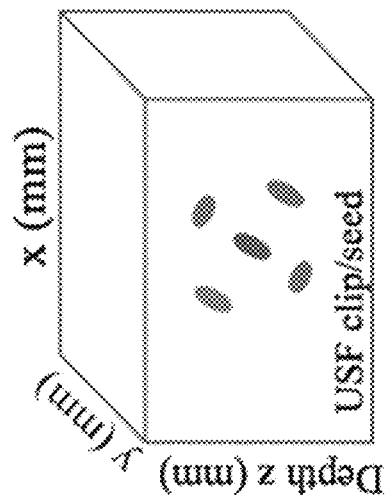

FIG. 16 illustrates an exemplary method of using multiplex USG imaging. As shown, multiple tissue implantation devices having different USF contrast agents with different peak emission wavelengths are implanted in breast tissue. A USF imaging probe, such as probe 11 in Example 5, can detect the different peak emission wavelengths from each device, and spatially resolve each device from each other in at least the xy plane, or in some cases, the xyz plane.

Various embodiments of the invention have been described in fulfillment of the various objectives of the invention. It should be recognized that these embodiments are merely illustrative of the principles of the invention. Numerous modifications and adaptations thereof will be readily apparent to those skilled in the art without departing from the spirit and scope of the invention.

The invention claimed is:

1. A method of imaging a tissue implantation device in a biological environment comprising:
  disposing two or more tissue implantation devices in a biological environment, the tissue implantation devices each comprising a capsule and a population of ultrasound-switchable fluorophores incorporated in the capsule, the population of ultrasound-switchable fluorophores having a switching threshold in the biological environment;
  exposing the biological environment to an ultrasound beam to form an activation region within the biological environment;

switching the ultrasound-switchable fluorophores in the activation region from an off state to an on state;

exciting the ultrasound-switchable fluorophores in the activation region with a beam of electromagnetic radiation;

detecting light emitted by the ultrasound-switchable fluorophores;

correlating a size, shape, position, orientation, or any combination thereof, of the two or more tissue implantation devices in the biological environment based on the detected light emitted by the ultrasound-switchable fluorophores; and resolving the two or more tissue implantation devices based on the detected light emitted by the ultrasound-switchable fluorophores, wherein the two or more tissue implantation devices are spatially resolved from each other in at least an xy plane.

2. The method of claim 1, wherein the beam of electromagnetic radiation is in the red or near-infrared region (NIR) of the electromagnetic spectrum.

3. The method of claim 1, wherein the ultrasound-switchable fluorophores in the activation region are excited by a single beam of electromagnetic radiation.

4. The method of claim 1, wherein light emitted by the ultrasound-switchable fluorophores has a peak emission wavelength in the infrared spectrum.

5. The method of claim 1, wherein the two or more tissue implantation devices comprise the same or different ultrasound-switchable fluorophores having the same or different peak emission wavelengths.

6. The method of claim 1, wherein the two or more tissue implantation devices comprise different ultrasound-switchable fluorophores having the same or different switching thresholds.

7. The method of claim 1, wherein each of the two or more tissue implantation devices is disposed at a depth of 0.1-10 centimeters (cm) below a surface of the biological environment.

8. A method of imaging a tissue implantation device in a biological environment comprising:

disposing two or more tissue implantation devices in a biological environment, the two or more tissue implantation devices comprising a capsule and a population of ultrasound-switchable fluorophores incorporated in the capsule, the population of ultrasound-switchable fluorophores having a switching threshold in the biological environment;

exposing the biological environment to an ultrasound beam to form an activation region within the biological environment;

switching the ultrasound-switchable fluorophores in the activation region from an off state to an on state;

exciting the ultrasound-switchable fluorophores in the activation region with a beam of electromagnetic radiation;

detecting light emitted by the ultrasound-switchable fluorophores; and resolving the two or more tissue implantation devices by detecting the light emitted by the ultrasound-switchable fluorophores, wherein the two or more tissue implantation devices are spatially resolved from each other in at least an xy plane.

* * * * *